(12) United States Patent
Fahim et al.

(10) Patent No.: US 6,696,065 B1
(45) Date of Patent: Feb. 24, 2004

(54) ACELLULAR PERTUSSIS VACCINES AND METHODS OF PREPARATION THEREOF

(75) Inventors: Raafat E. F. Fahim, Mississauga (CA); Larry U. L. Tan, Mississsauga (CA); Luis Barreto, Concord (CA); John Thipphawong, Toronto (CA); Gail E. D. Jackson, Richmond Hill (CA)

(73) Assignee: Aventis Pastuer Limited, Toronto (CA)

( * ) Notice: Subject to any disclaimer, the term of this patent is extended or adjusted under 35 U.S.C. 154(b) by 0 days.

(21) Appl. No.: 08/672,530

(22) Filed: Jul. 2, 1996

Related U.S. Application Data

(63) Continuation-in-part of application No. 08/501,743, filed on Jul. 12, 1995, which is a continuation-in-part of application No. 08/433,646, filed on May 4, 1995.

(51) Int. Cl.$^7$ .................. A61K 39/10; A61K 39/00; A61K 39/38; A61K 33/00
(52) U.S. Cl. .................. 424/254.1; 424/184.1; 424/241.1; 424/242.1; 424/253.1; 424/236.1; 424/689; 424/690; 424/698; 435/7.2; 435/7.3
(58) Field of Search .................. 424/241.1, 242.1, 424/253.1, 254.1, 184.1, 236.1, 689, 690, 698; 435/7.2, 7.3

(56) References Cited

U.S. PATENT DOCUMENTS

| | | | | |
|---|---|---|---|---|
| 4,997,915 | A | * | 3/1991 | Tan et al. |
| 5,776,468 | A | * | 7/1998 | Hauser et al. |
| 6,013,264 | A | * | 1/2000 | Petre et al. |
| 6,399,076 | B2 | * | 6/2002 | Vose et al. |
| 2003/0022304 | A1 | * | 1/2003 | Artois et al. ............ 435/69.1 |

FOREIGN PATENT DOCUMENTS

| | | |
|---|---|---|
| EP | 0484612 | 5/1992 |
| GB | 928807 | 6/1963 |
| WO | WO 93/24148 | 12/1993 |
| WO | WO 96/34623 | 11/1996 |
| WO | WO 96/40242 | 12/1996 |
| WO | WO 97/00697 | 1/1997 |

OTHER PUBLICATIONS

Cameron, J. Dev. Biol. Stand. 24:155–65 (see abstract), 1974.*
Bosy et al Lancet, 339:8792:507–510, 1992.*
Dagan et al. ASM Mtg. 1996 p. 154 Abstract# G59.*
Cherry. Vaccine 10/14:1033–1038, 1992.*
Goldenthal. Anno N.Y. Acad. Sci 754:xi–xv, 1995.*
Gustafsson et al. N. Eng. J. Med. 334:349–55, 1996.*
Edwards et al. Pediatr. Infect. Dis. J. 13/5:345–47, 1994.*
Dagan et al, Pediatr. Infect. Dis. J. 16/12:1113–1121, 1997.*
Edwards et al Pediatr Infect. Dis. J. 16/4:S97–S102, 1997.*
Parkman et al. Recent Advances in Immunization ed. Halsey et al pp 65–80, 1983.*
Schmit et al ICAAG Mtg. 1997 Abstract # G–92.*
David et al, ICAAG Mtg 1991 Abstract # 60, 1991.*
Van Wezel, et al, Reviews of Infectious Dis. 6/Suppl 2:S335–S340, 1984.*
Halperin et al, Ann. NY Acad. Sci. 754:89–96, 1995.*
Baker et al, J Pediatr, 121:523–27, 1992.*
Granoff, Pediatr Infect Dis J., 1996, 15:1069–1070.
Gold, Ronald, et al; Safety and immunogenicity of Haemophilus influenzae vaccine (tetanus toxoid conjugate) administered concurrently or combined with diphtheria and tetanus toxoids, pertussis vaccine and inactivated poliomyelitis vaccine to healthy infants at two, four and six months of age—Pediatr. Infect. Dis. J. 1994: 13: 348–55.
Plotkin, S.A., and Orenstein, W.A.,—Vaccines—Third Edition—1999.
Insel, R.A.—Potential Alterations in Immunogenicity by Combining or Simultaneously Administering Vaccine Components, pp. 35–47.
Frey, S., et al—Interference of Antibody Production to Hepatitis B Surface Antigen in a Combination Hepatitis A/Hepatitis B Vaccine—Journal of Inf. Dis.—1999: 180: 2018–22.
Ambfrosch, F. et al—Combined Vaccination Against Yellow Fever and Typhoid Fever: a comparative trial; Vaccine 1994 vol. 12, No. 7; pp. 625–628.
Fattom, A. et al—Epitopic overload at the site of injection may result in suppression of the immune response to combined capsular polysaccharide conjugate vaccines—Vaccine 17 (1999) 126–133.

* cited by examiner

*Primary Examiner*—Nita Minnifield
(74) *Attorney, Agent, or Firm*—Gavin Zealey

(57) ABSTRACT

A multi-component vaccine composition is described comprising acellular pertussis vaccine components, diphtheria toxoid, tetanus toxoid and inactivated poliovirus. The composition also may contain a conjugate of a capsular polysaccharide on *Haemophilus influenzae* type b and tetanus toxoid or diphtheria toxoid, which may be reconstituted from a lyophilized state by the other component. The administration of the multiple component vaccine resulted in no diminution of the immunogenicity of any component as a result of interference by other components of the vaccine.

10 Claims, 1 Drawing Sheet

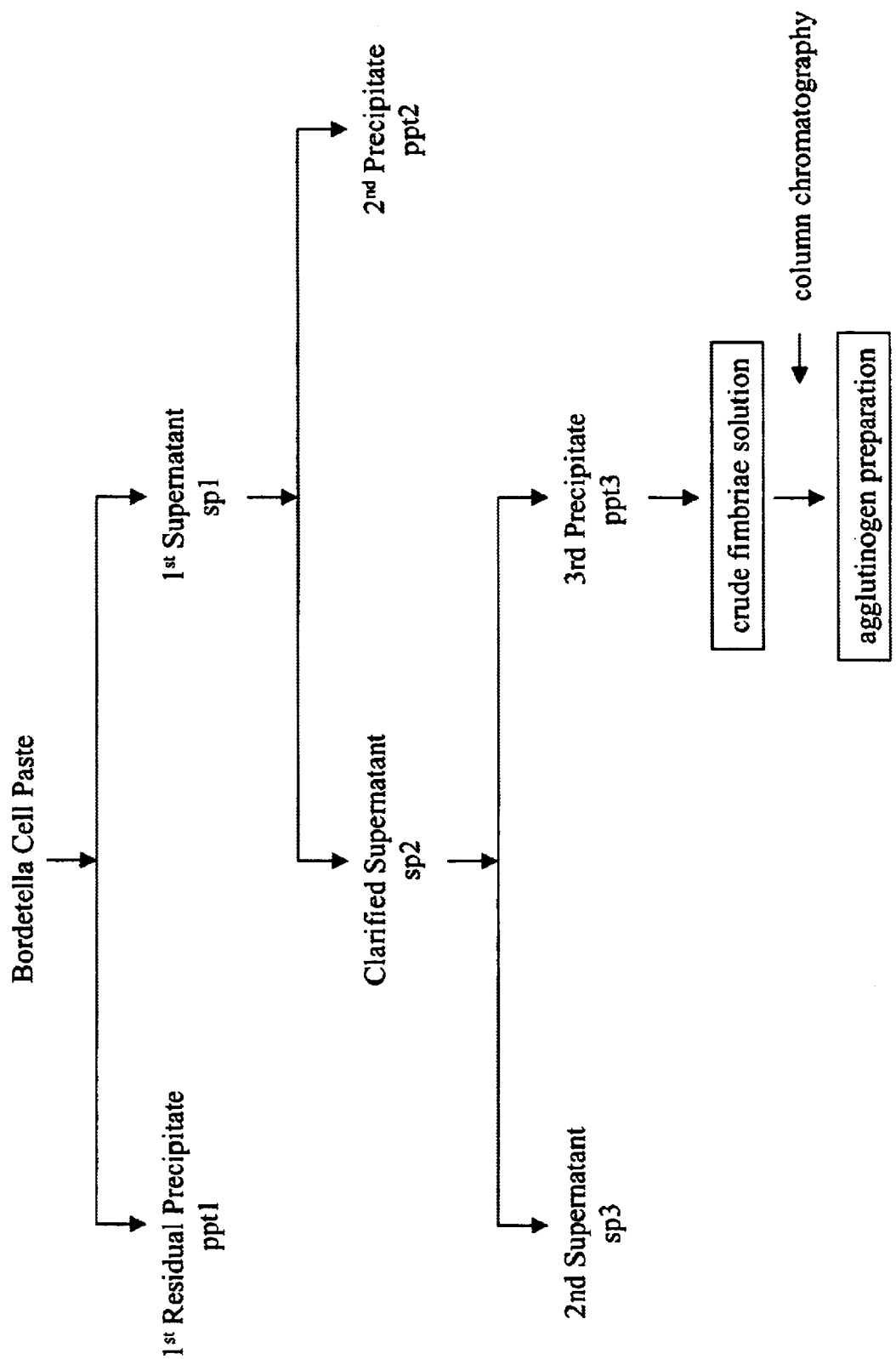
Figure 1: Isolation of an Agglutinogen Preparation

ACELLULAR PERTUSSIS VACCINES AND METHODS OF PREPARATION THEREOF

REFERENCE TO RELATED APPLICATION

This application is a continuation-in-part of U.S. patent application Ser. No. 08/501,743, filed Jul. 12, 1995, which itself is a continuation-in-part of U.S. patent application Ser. No. 08/433,646 filed May 4, 1995.

FIELD OF INVENTION

The present invention relates to acellular pertussis vaccines, components thereof, and their preparation.

BACKGROUND TO THE INVENTION

Whooping cough or pertussis is a severe, highly contagious upper respiratory tract infection caused by *Bordetella pertussis*. The World Health Organization estimates that there are 60 million cases of pertussis per year and 0.5 to 1 million associated deaths (ref. 1). Throughout this specification., various references are referred to in parenthesis to more fully describe the state of the art to which this invention pertains. Full bibliographic information for each citation is found at the end of the specification, immediately following the claims. The disclosures of these references are hereby incorporated by reference into the present disclosure). In unvaccinated populations, a pertussis incidence rate as high as 80% has been observed in children under 5 years old (ref. 2). Although pertussis is generally considered to be a childhood disease, there is increasing evidence of clinical and asymptomatic disease in adolescents and adults (refs. 3, 4 and 5).

The introduction of whole-cell vaccines composed of chemically- and heat-inactivated *B. pertussis* organisms in the 1940's was responsible for a dramatic reduction in the incidence of whooping cough caused by *B. pertussis*. The efficacy rates for whole-cell vaccines have been estimated at up to 95% depending on case definition (ref. 6). While infection with *B. pertussis* confers life-long immunity, there is increasing evidence for waning protection after immunization with whole-cell vaccines (ref. 3). Several reports citing a relationship between whole-cell pertussis vaccination, reactogenicity and serious side-effects led to a decline in vaccine acceptance and consequent renewed epidemics (ref. 7). More recently defined component pertussis vaccines have been developed.

Antigens for Defined Pertussis Vaccines

Various acellular pertussis vaccines have been developed and include the *Bordetella pertussis* antigens, Pertussis Toxin (PT), Filamentous haemagglutonin (FHA), the 69 kDa outer membrane protein (pertactin) and fimbrial agglutinogens (see Table 1 below. The Tables appear at the end of the specification).

Pertussis Toxin

Pertussis toxin is an exotoxin which is a member of the A/B family of bacterial toxins with ADP-ribosyltransferase activity (ref. 8). The A-moiety of these toxins exhibit the ADP-ribosyltransferase activity and the B portion mediates binding of the toxin to host cell receptors and the translocation of A to its site of action. PT also facilitates the adherence of *B. pertussis* to ciliated epithelial cells (ref. 9) and also plays a role in the invasion of macrophages by *B. pertussis* (ref. 10).

All acellular pertussis vaccines have included PT, which has been proposed as a major virulence factor and protective antigen (ref. 11, 12). Natural infection with *B. pertussis* generates both humoral and cell-mediated responses to PT (refs. 13 to 17). Infants have transplacentally-derived anti-PT antibodies (refs. 16, 18) and human colostrum containing anti-PT antibodies was effective in the passive protection of mice against aerosol infection (ref. 19). A cell-mediated immune (CMI) response to PT subunits has been demonstrated after immunization with an acellular vaccine (ref. 20) and a CMI response to PT was generated after whole-cell vaccination (ref. 13). Chemically-inactivated PT in whole-cell or component vaccines is protective in animal models and in humans (ref. 21) Furthermore, monoclonal antibodies specific for subunit S1 protect against *B. pertussis* infection (refs. 22 and 23).

The main pathophysiological effects of PT are due to its ADP-ribosyltransferase activity. PT catalyses the transfer of ADP-ribose from NAD to the $G_i$ guanine nucleotide-binding protein, thus disrupting the cellular adenylate cyclase regulatory system (ref. 24). PT also prevents the migration of macrophages and lymphocytes to sites of inflammation and interferes with the neutrophil-mediated phagocytosis and killing of bacteria (ref. 25). A number of in vitro and in vivo assays have been used to asses the enzymatic activity of S1 and/or PT, including the ADP-ribosylation of bovine transducin (ref. 26), the Chinese hamster ovary (CHO) cell clustering assay (ref. 27), histamine sensitization (ref. 28), leukocytosis, and NAD glycohydrolase. When exposed to PT, CHO cells develop a characteristic clustered morphology. This phenomenon is dependent upon the binding of PT, and subsequent translocation and ADP-ribosyltransferase activity of S1 and thus the CHO cell clustering assay is widely used to test the integrity and toxicity of PT holotoxins.

Filamentous Haemagglutinin

Filamentous haemagglutinin is a large (220 kDa) non-toxic polypeptide which mediates attachment of *B. pertussis* to ciliated cells of the upper respiratory tract during bacterial colonization (refs. 9, 29). Natural infection induces anti-FHA antibodies and cell mediated immunity (refs. 13, 15, 17, 30 and 31). Anti-FHA antibodies are found in human colostrum and are also transmitted transplacentally (refs. 17, 18 and 19). Vaccination with whole-cell or acellular pertussis vaccines generates anti-FHA antibodies and acellular vaccines containing FHA also induce a CMI response to FHA (refs. 20, 32). FHA is a protective antigen in a mouse respiratory challenge model after active or passive immunization (refs. 33, 34). However, alone FHA does not protect in the mouse intracerebral challenge potency assay (ref. 28).

69 kDa Outer Membrane Protein (Pertactin)

The 69 kDa protein is an outer membrane protein which was originally identified from *B. bronchiseptica* (ref. 35). It was shown to be a protective antigen against *B. bronchiseptica* and was subsequently identified in both *B. pertussis* and *B. parapertussis*. The 69 kDa protein binds directly to eukaryotic cells (ref. 36) and natural infection with *B. pertussis* induces an anti-P.69 humoral response (ref. 14) and P.69 also induces a cell-mediated immune response (ref. 17, 37, 38). Vaccination with whole-cell or acellular vaccines induces anti-P.69 antibodies (refs. 32, 39) and acellular vaccines induce P.69 CMI (ref. 39). Pertactin protects mice against aerosol challenge with *B. pertussis* (ref. 40) and in combination with FHA, protects in the intracerebral challenge test against *B. pertussis* (ref. 41). Passive transfer of polyclonal or monoclonal anti-P.69 antibodies also protects mice against aerosol challenge (ref. 42).

Agglutinogens

Serotypes of *B. pertussis* are defined by their agglutinating fimbriae. The WHO recommends that whole-cell vaccines include types 1, 2 and 3 agglutinogens (Aggs) since they are not cross-protective (ref. 43). Agg 1 is non-fimbrial and is found on all *B. pertussis* strains while the serotype 2 and 3 Aggs are fimbrial. Natural infection or immunization with whole-cell or acellular vaccines induces anti-Agg antibodies (refs. 15, 32). A specific cell-mediated immune response can be generated in mice by Agg 2 and Agg 3 after aerosol infection (ref. 17). Aggs 2 and 3 are protective in mice against respiratory challenge and human colostrum containing anti-agglutinogens will also protect in this assay (refs. 19, 44, 45).

Acellular Vaccines

The first acellular vaccine developed was the two-component PT+FHA vaccine (JNIH 6) of Sato et al. (ref. 46). This vaccine was prepared by co-purification of PT and FHA antigens from the culture supernatant of *B. pertussis* strain Tohama, followed by formalin toxoiding. Acellular vaccines from various manufacturers and of various compositions have been used successfully to immunize Japanese children against whopping cough since 1981 resulting in a dramatic decrease in incidence of disease (ref. 47). The JNIH 6 vaccine and a mono-component PT toxoid vaccine (JNIH 7) were tested in a large clinical trial in Sweden in 1986. Initial results indicated lower efficacy than the reported efficacy of a whole-cell vaccine, but follow-up studies have shown it to be more effective against milder disease diagnosed by serological methods (refs. 48, 49, 50, 51). However, there was evidence for reversion to toxicity of formalin-inactivated PT in these vaccines. These vaccines were also found to protect against disease rather than infection.

A number of new acellular pertussis vaccines are currently being assessed which include combinations of PT, FHA, P.69, and/or agglutinogens and these are listed in Table 1. Several techniques of chemical detoxication have been used for PT including inactivation with formalin (ref. 46), glutaraldehyde (ref. 52), hydrogen peroxide (ref. 53), and tetranitromethane (ref. 54).

Poliomyelitis

Both inactivated (IPV) and live attenuated (OPV) poliovirus vaccines have been effective in controlling poliomyelitis worldwide. A combined DPT-IPV vaccine is currently licensed in Europe and in Canada and has been shown to be safe and effective in millions of children worldwide.

*Haemophilus influenzae* type b

Prior to the availability of effective vaccines, *Haemophilus influenzae* type b was a major cause of meningitis invasive bloodborne infections in young children and was the main cause of meningitis in the first 2 years of life (ref. 80). Approximately 10% of *Haemophilus influenzae* meningitis victims die despite medical care. Permanent sequelae are common in survivors. Immunization against *Haemophilus influenzae* began in Canada in 1987 with a polysaccharide vaccine (polyribose ribitol phosphate *Haemophilus influenzae* type b [PRP]). Improved immunogenicity was achieved in children 18 months of age and older with the introduction in 1988 of a vaccine consisting of PRP conjugated to diphtheria toxoid (PRP-D). Since 1992, infant immunization has been possible with the licensure of PRP conjugate vaccines immunogenic in infants under 1 year of age (PRP conjugated with tetanus toxoid or PRP-T). The use of these *Haemophilus influenzae* conjugate vaccines has been associated with a dramatic decrease in the incidence of invasive Haemophilus infection in Canada and elsewhere (ref. 81). Two Canadian clinical studies involving nearly 900 children in British Columbia and Alberta demonstrated that lyophilized PRP-T may be reconstituted with DPT (COMBIPAC) (ref. 82) or with DPT-Polio Adsorbed (PENTA™) (Ref. 83) in addition to the usual saline diluent. Clinical studies involving more than 100,000 children around the world have demonstrated the efficacy of lyophilized PRP-T (ActHib™). Over 90% achieve anti-PRP levels considered to be protective ($\geq 0.15$ µg/ml) after 3 doses of PRP-T starting at 2 months or after a single dose of PRP-T given after 12 months of age. The proportion achieving levels indicative of long term protection (>1.0 µg/ml) varies from 70 to 100% depending on the study. Millions of doses of PRP-T have been sold in Canada since 1992. Breakthrough cases of invasive haemophilus infection after vaccination with PRP-T are rare and may be associated with diseases such as immunodeficiency (ref. 84).

Combination Vaccines

Although there are many actual and potential benefits of vaccines that combine antigens to confer protection against multiple pathogens, these combinations may have a detrimental effect on the immunogenicity of the individual components. Combinations of diphtheria and tetanus toxoids with whole cell pertussis vaccine (DTP) have been available for over 50 years and the antibody response to the combination is superior to the individual components, perhaps as a result of an adjuvant effect of the whole cell pertussis vaccine. DTP combinations that also include inactivated poliovirus vaccine are licensed in many jurisdictions, although the antibody response to the pertussis antigens may be diminished by this combination (ref 69–71). The effect of combining DTP vaccines with Hib conjugate vaccine have been variable. Studies with a French DTP and PRPT demonstrated similar safety but a decreased antibody response to PRP (ref. 72–73) whereas studies with a Canadian DTP and PRPT vaccine showed no effect on the PRP response but lower pertussis agglutinins and increased injection site tenderness in the combined immunization group (ref 74, 75).

Data are now becoming available on the effect of combining APDT vaccines with Hib conjugate vaccine. In two month old infants given three doses of an acellular pertussis-diphtheria-tetanus vaccine (APDT) combined with a Hib conjugate vaccine (PRPT), the antibody, response to PRP was significantly lower than in the group given separate injections on the same day (ref. 76). Similar results were reported with another acellular pertussis-diphtheria-tetanus vaccine combined with PRPT given for the first three doses (ref 77).

In contrast to other reported studies, children immunized with the combined vaccine had a superior antibody response to PRP, diphtheria, and several of the pertussis antigens when compared to children given PRP at a separate visit. There may be several reasons for the equivalent or better immunogenicity for these vaccines when given as a combined injection rather than the decreased immunogenicity reported with other products. All acellular pertussis vaccines are not identical in their antigenic content, method of toxoiding, adjuvant or preservative. However, decreased immunogenicity has been reported with acellular pertussis vaccines containing PT, FHA, and 69K (ref. 77) and with containing PT, FHA, 69K and fimbriae (ref. 76).

The five component APDT examined in this study was found to have a protective efficacy of 85% (example 5) (95% CI 81/89) in a phase III clinical trial recently completed in Sweden under the auspices of the National Institutes of Health (ref. 78). This study demonstrated that this vaccine can be combined with Hib-tetanus toxoid conjugate vaccine as a single injection for the fourth dose in children between 17 and 21 months of age.

Current commercially-available combination vaccines may not contain appropriate formulations of appropriate antigens in appropriate immunogenic forms to achieve a desired level of efficacy in a pertussis-susceptible human population.

It would be desirable to provide efficacious combination vaccines comprising acellular pertussis components containing selected relative amounts of selected antigens.

SUMMARY OF THE INVENTION

The present invention is directed towards combination vaccines containing acellular pertussis vaccine components, and methods of use thereof.

In accordance with one aspect of the present invention, there is provided a multi-valent immunogenic composition for conferring protective in a host against disease caused by infection by *Bordetella pertussis, Clostridium tetani, Corynebacterium diphtheriae,* poliovirus and/or *Haemophilus influenzae,* comprising:

(a) pertussis toxoid, filamentous haemagglutinin, pertactin and agglutinogens in purified form, (b) tetanus toxoid, (c) diphtheria toxoid, (d) inactivated polio virus, and, optionally, (e) a conjugate of a carrier molecule selected from tetanus toxoid and diphtheria toxoid and a capsular polysaccharide of *Haemophilus influenzae* type b.

The immunogenic compositions may be formulated as a vaccine for in vivo administration to the host wherein the individual components of the composition are formulated such that the immunogenicity of individual components is not impaired by other individual components of the composition.

In immunogenic composition may further comprise an adjuvant, particularly aluminum hydroxide or aluminum phosphate.

Such vaccine composition may contain about 5 to about 30 μg nitrogen of pertussis toxoid, about 5 to about 30 μg nitrogen of filamentous haemagglutinin, about 3 to about 15 μg nitrogen of pertactin and about 1 to about 10 μg nitrogen of agglutinogens.

In one specific embodiment, the vaccine may comprise pertussis toxoid, fimbrial haemagglutinin, the 69 kDa protein and filamentous agglutinogens of *Bordetella pertussis* at a weight ratio of about 10:20:5:3 as provided by about 20 μg of pertussis toxoid, about 20 μg of filamentous haemagglutinin, about 5 μg of fimbrial agglutinogens and about 3 μg of fimbrial 69 Kda protein in a single human dose. In one embodiment of the vaccine provided herein, the vaccine contains about 15 Lfs of diphtheria toxoid and about 5 Lfs of tetanus toxoid.

The inactivated poliovirus employed in the immunogenic composition of the invention generally comprises a mixture of inactivated poliovirus types 1,2 and 3. In one formulation, such mixtures of inactivated poliovirus types may comprise:

about 40 D antigen units of piliovirus type 1 about 8 D antigen units of poliovirus type 2 about 32 D antigen units of poliovirus type 3 in a single human dose.

The conjugate molecule may comprise a conjugate of toxoid or diphtheria toxoid and polyribose ribitol phosphate (PRP) of *Haemophilus influenzae* type b. Such conjugate molecule may be provided in a hydrolyzed form, which is reconstituted for administration by combination with the other components. In one formulation, the conjugate is employed in the form of about 10 μg of PRP conjugate to about 20 μg of tetanus toxoid.

In addition, the vaccine may also comprise an adjuvant, particularly aluminum phosphate.

In such particular embodiments, the immunogenic compositions provide an immune response profile to each of the pertussis antigens contained therein and the response profile provided by the acellular components is substantially equivalent to that produced by a whole cell pertussis vaccine.

In a further aspect of the invention, there is provided a method of immunizing a host against multiple diseases, comprising administering to the host, which may be human, an immunoeffective amount of the immunogenic composition or vaccine as provided herein.

Advantages of the present invention include a multi-valent vaccine which can confer protection against a range of common pediatric diseases in a safe and efficacious manner. The ability to provide a single vaccination against multiple diseases without interference between the immunogenic responses to the various immunogens is beneficial.

BRIEF DESCRIPTION OF THE DRAWINGS

The present invention will be further understood from the following detailed description and Examples with reference to the accompanying drawing in which:

FIG. 1 is a schematic flow sheet of a procedure for the isolation of an agglutinogen preparation from a Bordetella strain.

DETAILED DESCRIPTION OF THE INVENTION

Agglutinogen Preparation

Referring to FIG. 1, there is illustrated a flow sheet of a method for preparing an agglutinogen preparation from a Bordetella strain. As seen in FIG. 1, a Bordetella cell paste containing the agglutinogens, such as *B. pertussis* cell paste, is extracted with, for example, a urea-containing buffer, such as 10 mM potassium phosphate, 150 mM NaCl and 4M urea, to selectively extract the agglutinogens from the cell paste to produce a first supernatant (sp1) containing agglutinogens and a first residual precipitate (ppt1). The first supernatant (sp1) is separated from the first residual precipitate (ppt1) such as by centrifugation. The residual precipitate (ppt1) is discarded. The clarified supernatant (sp1) then may be concentrated and diafiltered against, for example, 10 mM potassium phosphate/150 mM NaCl/0.1% Triton X-100 using, for example, a 100 to 300 kDa NMWL membrane filter.

The first supernatant then is incubated at a temperature and for a time to produce a clarified supernatant (sp2) containing agglutinogens and a second discard precipitate (ppt2) containing non-agglutinogen contaminants. Appropriate temperatures include about 50° C. to about 100° C., including about 75° to about 85° C., and appropriate incubation times include about 1 to about 60 minutes. The clarified supernatant then is concentrated by, for example, the addition of polyethylene glycol of molecular weight about 8000 (PEG 8000) to a final concentration of about 4.5±0.2% and stirring gently for a minimum of about 30 minutes to produce a third precipitate (ppt3) which may be collected by centrifugation. The remaining supernatant sp3 is discarded.

This third precipitate (ppt3) is extracted with, for example, a buffer comprising 10 mM potassium phosphate/ 150 mM NaCl to provide the crude fimbrial agglutinogen-containing solution. 1M potassium phosphate may be added to the crude fimbrial solution to make it about 100 mM with respect to potassium phosphate. Alternatively, the clarified supernatant of heat-treated fimbrial agglutinogens can be purified without precipitation by gel-filtration chromatography using a gel, such as Sepharose CL6B. The fimbrial agglutinogens in the crude solution then are purified by column chromatography, such as, by passing through a PEI silica column, to produce the fimbrial agglutinogen preparation in the run-through.

This fimbrial agglutinogen containing run-through may be further concentrated and diafiltered against, for example, a buffer containing 10 mM potassium phosphate/150 mM NaCl using a 100–300 kDa NMWL membrane. The agglutinogen preparation may be sterilized by filtration through a $\leq 0.22$ $\mu$M membrane filter, to provide the final purified fimbrial agglutinogen preparation containing fimbrial agglutinogen 2 and 3 substantially free from agglutinogen 1. The weight ratio of Agg 2 to Agg 3 may be from about 1.5:1 to about 2:1. The present invention extends to immunogenic compositions (including vaccines) comprising the fimbrial agglutinogen preparations as provided herein along with other components. Such vaccines contain other purified Bordetella immunogens including filamentous haemagglutinin, the 69 kDa outer membrane protein and pertussis toxin or a toxoid thereof, including genetically detoxified analogs of PT as described in, for example, ref. 68.

The other Bordetella immunogens, pertussis toxin (including genetically detoxified analogs thereof, as described in, for example, Klein et al, U.S. Pat. No. 5,085,862 assigned to the assignee hereof and incorporated herein by reference thereto), FHA and the 69 kDa protein may be produced by a variety of methods such as described below:

Purification of PT

PT may be isolated from the culture supernatant of a *B. pertussis* strain using conventional methods. For example, the method of Sekura et al (ref. 55) may be used. PT is isolated by first absorbing culture supernatant onto a column containing the dye-ligand gel matrix, Affi-Gel Blue (Bio-Rad Laboratories, Richmond, Calif.). PT is eluted from this column by high salt, such as, 0.75 M magnesium chloride and, after removing the salt, is passed through a column of fetuin-Sepharose affinity matrix composed of fetuin linked to cyanogen bromide-activated Sepharose. PT is eluted from the fetuin column using 4M magnesium salt.

Alternatively, the method of Irons et al (ref. 56) may be used. Culture supernatant is absorbed onto a CNBr-activated Sepharose 4B column to which haptoglobin is first covalently bound. The PT binds to the absorbent at pH 6.5 and is eluted from the column using 0.1M Tris/0.5M NaCl buffer by a stepwise change to pH 10.

Alternatively, the method described in U.S. Pat. No. 4,705,686 granted to Scott et al on Nov. 10, 1987 and incorporated herein by reference thereto may be used. In this method culture supernatants or cellular extracts of *B. pertussis* are passed through a column of an anion exchange resin of sufficient capacity to adsorb endotoxin but permit Bordetella antigens to flow through or otherwise be separated from the endotoxin.

Alternatively, PT may be purified by using perlite chromatography, as described in EP Patent No. 336 736, assigned to the assignee hereof and incorporated herein by reference thereto.

Detoxification of PT

PT is detoxified to remove undesired activities which could cause side reactions of the final vaccine. Any of a variety of conventional chemical detoxification methods can be used, such as treatment with formaldehyde, hydrogen peroxide, tezranitro-methane, or glutaraldehyde.

For example, PT can be detoxified with glutaraldehyde using a modification of the procedure described in Munoz et al (ref. 57). In this detoxification process purified PT is incubated in a solution containing 0.01 M phosphate buffered saline. The solution is made 0.05% with glutaraldehyde and the mixture is incubated at room temperature for two hours, and then made 0.02 M with L-lysine. The mixture is further incubated for two hours at room temperature and then dialyzed for two days against 0.01 M PBS. In a particular embodiment, the detoxification process of EP Patent No. 336 736 may be used. Briefly PT may be detoxified with glutaraldehyde as follows:

Purified PT in 75 mM potassium phosphate at pH 8.0 containing 0.22M sodium chloride is diluted with an equal volume of glycerol to protein concentrations of approximately 50 to 400 $\mu$g/ml. The solution is heated to 37° C. and detoxified by the addition of glutaraldehyde to a final concentration of 0.5% (w/v). The mixture is kept at 37° C. for 4 hrs and then aspartic acid (1.5 M) is added to a final concentration of 0.25 M. The mixture is incubated at room temperature for 1 hour and then diafiltered with 10 volumes of 10 mM potassium phosphate at pH 8.0 containing 0.15M sodium chloride and 5% glycerol to reduce the glycerol and to remove the glutaraldehyde. The PT toxoid is sterile-filtered through a 0.2 $\mu$M membrane.

If recombinant techniques are used to prepare a PT mutant molecule which shows no or little toxicity, for use as the toxoided molecule, chemical detoxification is not necessary.

Purification of FHA

FHA may be purified from the culture supernatant essentially as described by Cowell et al (ref. 58). Growth promoters, such as methylated beta-cyclodextrins, may be used to increase the yield of FHA in culture supernatants. The culture supernatant is applied to a hydroxylapatite column. FHA is adsorbed onto the column, but PT is not. The column is extensively washed with Triton X-100 to remove endotoxin. FHA is then eluted using 0.5M NaCl in 0.1M sodium phosphate and, if needed, passed through a fetuin-Sepharose column to remove residual PT. Additional purification can involve passage though a Sepharose CL-6B column.

Alternatively, FHA may be purified using monoclonal antibodies to the antigen, where the antibodies are affixed to a CNBr-activated affinity column (ref. 59).

Alternatively, FHA may be purified by using perlite chromatography as described in the above-mentioned EP 336 736.

Purification of 69 kDa Outer Membrane Protein (pertactin)

The 69 kDa outer membrane protein (69K or pertactin) may be recovered from bacterial cells by first inactivating the cells with a bacteriostatic agent, such as thimerosal, as described in published EP 484 621 and incorporated herein by reference thereto. The inactivated cells are suspended in an aqueous medium, such as PBS (pH 7 to 8) and subjected to repeated extraction at elevated temperature (45 to 60° C.) with subsequent cooling to room temperature or 4° C. The extractions release the 69K protein from the cells. The material containing the 69K protein is collected by precipitation and passed through an Affi-gel Blue column. The 69K protein is eluted with a high concentration of salt, such as 0.5M magnesium chloride. After dialysis, it is passed through a chromatofocusing support.

Alternatively, the 69 kDa protein may be purified from the culture supernatant of a *B. pertussis* culture, as described in published PCT Application WO 91/15505, in the name of the assignee hereof and incorporated herein by reference thereto.

Other appropriate methods of purification of the 69 kDa outer membrane protein from *B. pertussis* are described in U.S. Pat. No. 5,276,142, granted to Gotto et al on Jan. 4, 1984 and in U.S. Pat. No. 5,101,014, granted to Burns on Mar. 31, 1992.

The vaccines also contain non-Bordetella immunogens including tetanus toxoid, diphtheria toxoid, inactivated poliovirus (IPV) and, optionally, a conjugate of diphtheria toxoid or tetanus toxoid tetanus toxoid, a capsular polysaccharide of *Haemophilus influenzae* type b. Other potential components of the multi-component vaccine include outer membrane protein of Haemophilus, hepatitis B surface antigen, mumps, measles and rubella.

Polyribose Phosphate (PRP) was isolated from *H. influenzae* type b, derivatized to provide an adipic acid dihydrazide and covalently conjugated to tetanus toxoid to provide PRP-T.

Each of the antigens is individually absorbed to an adjuvant (such as aluminum phosphate or aluminum hydroxide, collectively termed alum) to provide for convenient and rapid production of vaccines containing selected relative amounts of these antigens in the vaccines as provide herein.

Selected Multi-Valent Vaccine Formulations

In selected embodiments, the invention provides vaccines with the following characteristics (μg proteins used herein are based on Kjedahl test results performed on purified concentrates and are expressed as μg of protein nitrogen), all of which may be administered by intramuscular injection:

(a) $CP_{20/20/5/3}$DT-mIPV (HYBRID)

One formulation provides a combination of component pertussis vaccine (CP) combined with diphtheria (D) and tetanus (T) toxoids and inactivated poliovirus (mIPV) was termed $CP_{20/20/5/3}$DT-mIPV (HYBRID). Each 0.5 ml human dose of $CP_{20/20/5/3}$DT-mIPV hybrid was formulated to contain about:

| | |
|---|---|
| 20 μg | Pertussis toxoid (PT) |
| 20 μg | Filamentous haemagglutonin (FHA) |
| 5 μg | Fimbrial agglutinogens 2 and 3 (FIMB) |
| 3 μg | Pertactin outer membrane protein (69 kDa) |
| 15 Lf | Diphtheria toxoid |
| 5 Lf | Tetanus toxoid |
| 40 D | antigen units Poliovirus type 1 |
| 8 D | antigen units Poliovirus type 2 |
| 32 D | antigen units Poliovirus type 3 |
| 1.5 mg | Aluminum phosphate |
| 0.6% | 2-phenoxyethanol, as preservative. |

(b) $CP_{20/20/5/3}$DT-mIPV (HYBRID) used to reconstitute PRP-T contains (per 0.5 ml dose):

| | |
|---|---|
| 20 μg | Pertussis toxoid (PT) |
| 20 μg | Filamentous haemagglutinin (FHA) |
| 5 μg | Fimbriae 2 and 3 (FIM) |
| 3 μg | Pertactin membrane protein (69 kDa) |
| 15 Lf | Diphtheria toxoid |
| 5 Lf | Tetanus toxoid |

10 μg of purified polyribose ribitol phosphate capsular polysaccharide (PRP) of *Haemophilus influenzae* type b covalently bound to 20 μg of tetanus toxoid

| |
|---|
| Poliovirus type 1 40 D antigen units |
| Poliovirus type 2 8 D antigen units |
| Poliovirus type 3 32 D antigen units |
| 1.5 mg Aluminum phosphate |
| 0.6% 2-phenoxyethanol. |

Clinical Trials

A number of clinical trials were performed in humans as described herein to establish the safety, non-reactogenicity and utility of component vaccines for protection against pertussis vaccines containing fimbrial agglutinogens prepared as described herein, for protection against pertussis. In particular, immune responses to each of the antigens contained in the vaccines (as shown, for example, in Table 3 below) were obtained. One particular acellular pertussis vaccine $CP_{10/5/5/3}$DT was analyzed in a large placebo-controlled, multi-centre, double-randomized clinical trial in an at-risk human population to estimate the efficacy of the vaccine against typical pertussis.

The case definition for typical pertussis disease was:

Twenty-one days or more of spasmodic cough, and either culture-confirmed *B. pertussis,* or serological evidence of Bordetella specific infection indicated by a 100% IgG or IgA antibody rise in ELISA against FHA or PT in paired sera, or if serological data is lacking, the study child has been in contact with a case of culture-confirmed *B. pertussis* in the household with onset of cough within 28 days before or after the onset of cough in the study child.

The results of this study showed $CP_{10/5/5/3}$DT to be about 85% efficacious in preventing pertussis as defined in the case definition for typical pertussis disease as described above. In the same study, a two-component pertussis acellular vaccine containing only PT and FHA was about 58% efficacious and a whole-cell pertussis vaccine was about 48% efficacious (see Table 4 below). In addition, the $CP_{10/5/5/3}$DT vaccine prevented mild pertussis defined as a cough of at least one day duration to an efficacy of about 77%. In particular, the profile of immune response obtained was substantially the same as that obtained following immunization with whole-cell pertussis vaccines which are reported to be highly efficacious against pertussis.

The safety and immunogenicity of component pertussis vaccines in combination with diphtheria and Tetanus adsorbed, *Haemophilus influenzae* type b tetanus toxoid conjugate vaccine and inactivated poliomyelitis vaccine grown on vero cells ($CP_{20/20/5/3}$DT-PRP-T-IPV) were compared with whole cell pertussis vaccine in combination with diphtheria and tetanus toxoids adsorbed and inactivated poliomyelitis vaccine in combination with diphtheria and tetanus toxoids adsorbed and inactivated poliomyelitis vaccine grown on MRC-5 cells (DPT-polio adsorbed) used to reconstitute lyophilized *Haemophilus influenzae* type b tetanus toxoid conjugates vaccine (PENTA™) or component vaccine pertussis vaccine in combination with diphtheria and tetanus toxoids adsorbed *Haemophilus influenzae* type b tetanus toxoid conjugate vaccine and inactivated poliomyelitis vaccine grown on MRC-5 cells ($CP_{20/20/5/3}$DT-mIPV) given separately from or used to reconstitute lyophilized *Haemophilus influenzae* type b tetanus toxoid conjugate vaccine (PRP-T) in children at 2, 4, 6 and 18 months of age.

This randomized controlled trial enrolled 897 two month old infants to receive one of 8 different vaccine arms:

$CP_{20/20/5/3}$DT-PRP-T-IPV (liquid); $CP_{20/20/5/3}$DT given concurrently but at different site from PRP-T; or the control vaccine, whole cell DPT-Polio used to reconstitute PRP-T (PENTA™).

All study vaccines were well tolerated. No significant differences in reaction rates were seen between the two types of recombinant pertussis combinations. Children who received the combined $CP_{20/20/5/3}$DT-mIPV used to reconstitute PRP_T had slightly higher rates of local reactions compared to the same products administered at different sites. All component pertussis combinations had consistently lower rates of local and systemic reactions than the whole cell combination. Differences in reaction rates between component pertussis and whole cell vaccines were most apparent in the 24 hours immediately after vaccination.

Both Component Pertussis combinations produced excellent responses to all antigens. In all situations pertussis PT, FHA and Pertactin responses were superior to responses seen to while cell combinations. No significant differences were seen between component and whole cell combinations. No significant differences were seen between component and while cell formulations for anti-PRP, diphtheria and polios 1 and 2. Both component pertussis formulations produced higher tetanus responses than PENTA™. Both component formulations produced similar serologic responses to all antigens except polio 3, for which $CP_{20/20/5/3}$DT-mIPV used to reconstitute PRP-T produced higher responses than $CP_{20/20/5/3}$DT-PRP-T-IPV. Method of administration did not affect serologic responses to any antigens except tetanus. In both combined and separate groups, 100% of children were protected (>0.01 EU/ml) against tetanus after 3 doses of vaccine.

Most importantly, all vaccine groups had good responses to PRP-T with 98.3% of children achieving levels >0.15 μg/ml and over 86.1% of children achieving levels >1.0 μg/ml. These figures are comparable to those observed in previous studies in which whole cell pertussis vaccine were used with PRP-T.

The serological responses are shown in Tables 5 to 7. (H-hybrid)

Safety and immunogenicity of Pertussis Vaccine in combination with Diphtheria and Tetanus toxoids adsorbed and inactivated poliomyelitis vaccine grown on MRC-5 cells ($CP_{20/20/5/3}$DT-mIPV) given separately from or used to reconstitute lyophilized *Haemophilus influenzae* type b tetanus toxoid conjugate vaccine (PRP-T) as compared with Connaught whole cell pertussis vaccine in combination with Diphtheria and Tetanus toxoids adsorbed and inactivated poliomyelitis vaccine grown on MRC-5 cells (DPT-polio adsorbed) used to reconstitute lyophilized *Haemophilus influenzae* type b tetanus toxoid conjugate vaccine (PENTA™) in children at 10–19 months of age.

This five armed study included a wholecell PENTA™ control arm and $CP_{20/20/5/3}$DT-mIPV used to reconstitute PRP-T. The fifth group were given $CP_{20/20/5/3}$DT-mIPV concurrently but at a different site from PRP-T. Four hundred and eighty-nine subjects received vaccine at 18–19 months of age of which 466 (95%) completed the study according to protocol. $CP_{20/20/5/3}$DT-mIPV used to reconstitute PRP-T was significantly less reactogenic than PENTA™ particularly within the first 24 hours after vaccination. The reconstituted product had slightly higher rates of local reactions than the separately administered product.

PENTA™ produced higher polio 1 responses than $CP_{20/20/5/3}$DT-mIPV used to reconstitute PRP-T. No significant differences were seen for anti-PRP, diphtheria, pertussis agglutinin, fimbriae, polio 2 or polio 3. $CP_{20/20/5/3}$DT-mIPV used to reconstitute PRP-T produced significantly higher pertussis PT,FHA and pertactin serologic responses. The three lots of $CP_{20/20/5/3}$DT-mIPV used to reconstitute PRP-T produced consistent serologic responses to all antigens tested. No significant differences were seen between $CP_{20/20/5/3}$DT-mIPV given separately versus used to reconstitute PRP-T except for with tetanus antitoxin (6.78 vs. 4.91 EU/ml).

This study demonstrated that $CP_{20/20/5/3}$DT-mIPV used to reconstitute PRP-T produced consistent serologic responses in three lots and was more immunogenic than PENTA™ for Pertussis responses. $CP_{20/20/5/3}$DT-mIPV also produced significantly lower rates of local and systemic reactions than PENTA™.

Safety and immunogenicity of Component Pertussis Vaccine combined with Diphtheria and Tetanus toxoids adsorbed and inactivated poliomyelitis vaccine grown on MRC-5 cells ($CP_{20/20/5/3}$DT-mIPV) were compared with Connaught whole cell pertussis vaccine in combination with Diphtheria and Tetanus toxoids adsorbed and inactivated poliomyelitis vaccine grown on MRC-5 cells (DPT-polio adsorbed) in children at 4–6 years of age.

One hundred and sixty-four subjects were randomly allocated in a 4 to 1 ratio to receive either $CP_{20/20/5/3}$DT-mIPV (n=131) or DPT-Polio (n=33). No significant or serious adverse events occurred in the study. $CP_{20/20/5/3}$DT-mIPV had consistently lower rates of both local and systemic reactions particularly in the 0–24 hour period. Local reactions were common for both groups with 97% of DPT-Polio and 76.9% of $CP_{20/20/5/3}$DT-mIPV recipients having some local reaction in the 0–24 hour period. $CP_{20/20/5/3}$DT-mIPV local reactions were usually mild or moderate. In contrast, more than half of DPT-Polio recipients had local reactions graded as severe. Injection site tenderness usually disappeared by 72 hours but redness or swelling tended to persist well into the 24–72 hour period.

Systemic reactions in the 0–24 hour period were less common in $CP_{20/20/5/3}$DT-mIPV recipients (38.5%) than in DPT-Polio recipients (90.9%). Systemic reactions in the 24–72 hour period were uncommon for both groups.

Diphtheria, tetanus, polio 2 and 3 responses were comparable between the two vaccines. DPT-Polio recipients had a significantly higher polio 1 response (15.462) than did $CP_{20/20/5/3}$DT-mIPV recipients (10,903). All subjects had excellent responses and would be considered protected against the above diseases. Serologic responses to all pertussis antigens were significantly higher in $CP_{20/20/5/3}$DT-mIPV recipients.

Safety and immunogenicity of Component Pertussis Vaccine in combination with Diphtheria and Tetanus toxoids adsorbed, *Haemophilus influenzae* type b tetanus toxoid conjugate vaccine and inactivated poliomyelitis vaccine grown on MRC-5 cells ($CP_{20/20/5/3}$DTPRP-T-mIPV) were compared with whole cell pertussis vaccine in combination with Diphtheria and Tetanus toxoids adsorbed and inactivated poliomyelitis vaccine grown on MRC-5 cells (DPT-polio adsorbed) used to reconstitute lyophilized *Haemophilus influenzae* type b tetanus toxoid conjugate vaccine (PENTA™) or Component Pertussis Vaccine in combination with Diphtheria and Tetanus toxoids adsorbed and inactivated Poliomyelitis vaccine grown on MRC-5 cells ($CP_{20/20/5/3}$DT-mIPV) used to reconstitute lyophilized *Haemophilus influenzae* type b tetanus toxoid conjugate vaccine (PRP-T) in children at 18–19 months of age.

The purpose of this three armed randomized controlled, single blinded study was to assess the safety and immunogenicity of two new acellular Pertussis combinations.

$CP_{20/20/5/3}$DT-PRP-T-IPV and $CP_{20/20/5/3}$DT-mIPV used to reconstitute PRP-T, with PENTA™ (whole cell pertussis DPT Polio used to reconstitute PRP-T) in children 18–19 months old. A total of 99 children; 33 in each of the three vaccine groups participated, of which 97 (98%) completed the study according to protocol.

No serious reactions were observed in this study. PENTA™ recipients were significantly more likely to experience moderate or severe local and systemic reactions than recipients of the other two vaccines. Differences were most pronounced at 24 hours and reached statistical significance for fever, redness, swelling, tenderness, fussiness, decreased activity and eating less. Reactions tended to be mild in children who received Component Pertussis combinations. No significant differences in reaction rates were seen between the two Component Pertussis formulations although fussiness was seen more frequently at 24 hours in those receiving $CP_{20/20/5/3}$DT-mIPV used to reconstitute PRP-T vs $CP_{20/20/5/3}$DT-PRP-T-IPV (18% vs 3%).

Serologic responses were satisfactory with 100% of participants achieving levels considered protective for diphtheria antitoxin ($\geq 0.01$ IU/ml), tetanus antitoxin ($\geq 0.01$ IU/ml) and anti PRP ($\geq 1.0 \mu g$/ml). Detectable neutralizing antibodies to polio types 1, 2 and 3 were seen in all participants post immunization.

Diphtheria responses were higher in PENTA™ recipients reflecting the higher antigen content of this vaccine (25 Lf vs 15 Lf).

Pertussis antibodies were consistently higher in the two Component Pertussis combinations versus PENTA™ reaching statistical significance for anti-PT, anti-FHA and anti-pertactin GMT responses. Anti-fimbrial and pertussis agglutinating antibodies were also higher in Component Pertussis recipients although the differences did not reach statistical significance.

In summary, this study showed that the two acellular Pertussis combinations $CP_{20/20/5/3}$DT-mIPV used to reconstitute PFP-T and $CP_{20/20/5/3}$DT-PRP-T-IPV were comparable and produced satisfactorily low reaction rates and high serologic responses when given as a booster to children at 18–19 months of age.

This five armed study was designed to examine the interaction between $CP_{20/20/5/3}$DT and two IPVs (grown on Vero cells or on MRC-5 cells). Both IPVs were combined as a single liquid product with $CP_{20/20/5/3}$DT-mIPV and $CP_{20/20/5/3}$DT-vIPV or given concurrently but at a separate injection site ($CP_{20/20/5/3}$DT+mIPV and $CP_{20/20/5/3}$DT+vIPV). A fifth study group received $CP_{20/20/5/3}$DT and OPV concurrently. All subjects received PRP-T at the post immunization blood draw. Anti-PRP responses were not assessed in this study.

STUDY DESIGN

| NUMBER | VISIT 1 (17–19 months) | VISIT 2 (+1 mnth) |
|---|---|---|
| 85 | 1. $CP_{20/20/5/3}$DT − mIPV (1 injection) | PRP-T |
| 85 | 2. $CP_{20/20/5/3}$DT + mIPV (2 injections) | PRP-T |
| 85 | 3. $CP_{20/20/5/3}$DT − vIPV (1 injection) | PRP-T |
| 85 | 4. $CP_{20/20/5/3}$DT + vIPV (2 injection) | PRP-T |
| 85 | 5. $CP_{20/20/5/3}$DT + OPV (1 injection) | PRP-T |

In general, there were no differences in the rates of adverse reactions reported after the MRC-5 or vero cell derived inactivated poliomyelitis vaccines, whether the vaccine was given as a separate injection or combined with the $CP_{20/20/5/3}$DT (HYBRID) vaccine.

No significant differences were seen between groups for PT, FHA and pertactin. Responses in children receiving $CP_{20/20/5/3}$DT (HYBRID) and OPV were slightly but not significantly higher than in children receiving $CP_{20/20/5/3}$DT (HYBRID) and Vero cell IPV for FIM, pertussis agglutinin, diphtheria and tetanus. Polio responses were generally comparable or higher in children receiving an IPV versus an OPV vaccine. All but one individual had pertussis agglutinin >1:64. All but one individual achieved diphtheria antitoxin levels $\geq 0.1$ U/ml and all achieved tetanus antitoxin levels $\geq 0.1$ EU/ml.

The results of this study demonstrated that $CP_{20/20/5/3}$DT (HYBRID) in combination with IPV (either NMC-5 or Vero cell) to be safe and immunogenic in children 17 to 19 months of age. The combination vaccines were at least as immunogenic as the vaccine given as separate injections and in some cases more immunogenic. Combining the vaccine as a single injection was not associated with a significant increase in local adverse reactions. No substantial differences were detected in the adverse reactions or immune response to the two IPV preparations either as separate injections or combined products. The inclusion of IPV did not increase the rate of adverse reactions compared to $CP_{20/20/5/3}$DT (HYBRID) given alone (i.e. with OPV).

Serological results are summarized in Table 8 (H=hybrid).

Safety and immunogenicity of two Component Pertussis Vaccines in combination with Diphtheria and Tetanus toxoids adsorbed ($CP_{20/20/5/3}$DT and $CP_{10/5/5/3}$DT) alone or in combination with *Haemophilus influenzae* type b conjugate vaccine in children 17–19 months of age.

The six armed study was designed to examine the interaction between both $CP_{10/5/5/3}$DT) and Hybrid $CP_{20/20/5/3}$DT) Component Pertussis formulations and *Haemophilus influenzae* Type B Conjugate Vaccine (PRP-T) in at 18–19 months of age.

Three schedules were used in which each of the component pertussis vaccines were used to reconstitute PRP-T, given concurrently but at a separate site from PRP-T or PRP-T was given 1 month after the component pertussis vaccine. All children received OPV at the first visit and were primed with the same components pertussis vaccine at 2, 4 and 6 months of age. All children had previously participated in the large safety study of these two vaccine formulations.

A total of 545 subjects were enrolled in the study of which 542 (99%) completed the study.

| NUMBER | VISIT 1 (17–19 months) | VISIT 2 (+1 month) | VISIT 3 (+2 mnths) |
|---|---|---|---|
| 154 | 1. $CP_{20/20/5/3}$DT used to reconstitute PRP-T | BLOOD + | Blood | — |
| 152 | $CP_{20/20/5/3}$DT given concurrently with PRP-T OPV | OPV | Blood | — |
| 159 | $CP_{20/20/5/3}$DT | | PRP-T | Blood |
| 27 | $CP_{10/5/5/3}$DT used to reconstitute PRP-T | BLOOD + | Blood | — |
| 29 | $CP_{10/5/5/3}$DT given concurrently with PRP-T | OPV | | |
| 21 | $CP_{10/5/5/3}$DT | | PRP-T | Blood |

Serologic responses were generally higher to most antigens when a component pertussis combination vaccine and PRP-T were given on the same day compared to on separate days (see Table 9).

Importantly, anti-PRP responses were not diminished when PRP-T was given separately versus combined with a component pertussis combination vaccine on the same day. Post immunization GMTs in children given the vaccines on separate days were significantly lower. Differences in anti-PRP responses between combined and separate injections were seen when subjects were stratified by component pertussis vaccine formulation. Recipients Of $CP_{20/20/5/3}DT$ (HYBRID) demonstrated lower anti-PRP levels when the vaccine was given combined rather than separately. These differences were not seen with the $CP_{10/5/5/3}DT$ recipients and the differences disappeared when the groups were combined. All participants achieved anti-PRP levels $\geq 0.15$ $\mu g/ml$ and over 98% of each group had level $\geq 1.0$ $\mu g/ml$. Only four (0.7%) participants in the study failed to achieve this level; three in the separate injections on separate days and one in the combined injection group. Over 82% of each group exceeded titers of 10 $\mu g/ml$ of anti-PRP antibody.

Of the local reactions elicited, only tenderness was reported more frequently in the combined group (27.8%) compared to the separate day vaccination group (16.7%). This rate was not different from that seen in the group given vaccines on the same day as separate injections (24.2%).

Overall, a systemic reaction was reported with similar frequency (60–62.1%) in participants of each of the vaccine groups. Fever was reported in approximately one third of the participants. Only fussiness was reported more commonly in the combined injection group (33.3%) compared to the separate injection (22.0%) or the separate day (22.8%) groups.

To summarize, concurrent administration of $CP_{10/5/5/3}DT$ or $CP_{20/20/5/3}DT$ and PRP-T on the same day did not interfere with anti-PRP responses but may actually have enhanced them. Serologic responses to other antigens were also excellent. Tetanus was the only antigen affected when the two vaccines were mixed together but all children had high levels of protection.

In summary of these clinical trial results, it can be seen that $CP_{20/20/5/3}DT$-mIPV used to reconstitute PRP-T produces comparable serologic responses to diphtheria, tetanus and polios 1, 2 and 3 compared to PENTA™. Anti-PRP responses are comparable or higher than those observed with PENTA™ at both infant and booster doses. Tetanus responses are lower than $CP_{20/20/5/3}DT$-mIPV used to reconstitute PRP-T when compared to $CP_{20/20/5/3}DT$-mIPV given separately from PRP-T, but this reduction is not clinically relevant. Consistent with other studies, Connaught's whole cell vaccine produces comparable or higher fimbrae and agglutinins responses than component pertussis vaccine, however, this whole cell vaccine is known to contain a highly immunogenic fimbrial component. All other pertussis responses were consistently higher with $CP_{20/20/5/3}DT$-mIPV used to reconstitute PRP-T than with PENTA™. Thus, the present invention provides the multi-valent immunogenic compositions in which the immune responses to the antigens are not diminished or impaired by the other components or their inclusion in the multi-valent vaccine. Diminished immune responses are sometimes referred to as interference.

In particular, for clinical trials, ($CP_{10/5/5/3}DT$-IPV grown on MRC5 cells for reconstitution with ActHib) (PRP-T) and A5I ($CP_{10/5/5/3}DT$ PRP-T IPV grown on Vero cells 3 $\mu g/ml$) were prepared.

Component pertussis antigens were individually adsorbed to aluminum phosphate 3 mg/ml in the absence of preservative.

PT is in 10 mM potassium phosphate, 0.15M NaCl, 5% Glycerol.

FHA is in 10 mM potassium phosphate, 0.5M NaCl.

69K is in 10 mM potassium phosphate, 0.15M NaCl.

Fimbria is in 10 mM potassium phosphate, 0.15M NaCl.

D was absorbed to aluminum phosphate (6.25 mg/ml) at a concentration of 300 Lf/ml. 2-phenoxyethanol is added as a preservative to 0.6%. T was adsorbed to aluminum phosphate (6.25 mg/ml) at a concentration of 300 Lf/mL. 2-phenoxyethanol is added to 0.6%.

The adsorbed component pertussis antigens were combined with adsorbed D and adsorbed T at a concentration of 3.65 doses/ml or 55% of the final volume. The 2-phenoxyethanol content was 0.6%. Prior to combination with mIPV or v-IPV/PRP-T, sterility, aluminum content and 2-phenoxyethanol content were confirmed. For 5 ml, m-IPV and 2-phenoxyethanol were added and diluted to final strength. For A5I, v-IPV, PRP-T and 2-phenoxyethanol were added and diluted to final strength.

Vaccine Preparation and Use

Thus, immunogenic compositions, suitable to be used as vaccines, may be prepared from the immunogens as disclosed herein. The vaccine elicits an immune response in a subject which produces antibodies.

Immunogenic compositions including vaccines may be prepared as injectibles, as liquid solutions or emulsions. The immunogens may be mixed with pharmaceutically acceptable excipients which are compatible with the immunogens. Such excipients may include water, saline, dextrose, glycerol, ethanol, and combinations thereof. The immunogenic compositions and vaccines may further contain auxiliary substances, such as wetting or emulsifying agents, pH buffering agents, or adjuvants to enhance the effectiveness thereof. Immunogenic compositions and vaccines may be administered parenterally, by injection subcutaneously or intramuscularly. The immunogenic preparations and vaccines are administered in a manner compatible with the dosage formulation, and in such amount as will be therapeutically effective, immunogenic and protective. The quantity to be administered depends on the subject to be treated, including, for example, the capacity of the immune system of the individual to synthesize antibodies, and, if needed, to produce a cell-mediated immune response. Precise amounts of active ingredient required to be administered depend on the judgment of the practitioner. However, suitable dosage ranges are readily determinable by one skilled in the art and may be of the order of micrograms of the immunogens. Suitable regimes for initial administration and booster doses are also variable, but may include an initial administration followed by subsequent administrations. The dosage may also depend on the route of administration and will vary according to the size of the host.

The concentration of the immunogens in an immunogenic composition according to the invention is in general about 1 to about 95%. Immunogenicity can be significantly improved if the antigens are co-administered with adjuvants, commonly used as 0.005 to 0.5 percent solution in phosphate buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes.

To efficiently induce humoral immune responses (HIR) and cell-mediated immunity (CMI), immunogens are often emulsified in adjuvants. Many adjuvants are toxic, inducing granulomas, acute and chronic inflammations (Freund's complete adjuvant, FCA), cytolysis (saponins and Pluronic polymer) and pyrogenicity, arthritis and anterior uveitis (LPS and MDP). although FCA is an excellent adjuvant and widely used in research, it is not licensed for use in human or veterinary vaccines because of its toxicity.

Desirable characteristics of ideal adjuvants include:
(1) lack of toxicity;
(2) ability to stimulate a long-lasting immune response;
(3) simplicity of manufacture and stability in long-term storage;
(4) ability to elicit both CMI and HIR to antigens administered by various routes;
(5) synergy with other adjuvants;
(6) capability of selectively interacting with populations of antigen presenting cells (APC);
(7) ability to specifically elicit appropriate $T_H1$ or $T_H2$ cell-specific immune responses; and
(8) ability to selectively increase appropriate antibody isotype levels (for example, IgA) against antigens.

U.S. Pat. No. 4,855,283 granted to Lockhoff et al on August 8, 1989 which is incorporated herein by reference thereto teaches glycolipid analogues including N-glycosylamides, N-glycosylureas and N-glycosylcarbamates, each of which is substituted in the sugar residue by an amino acid, as immuno-modulators or adjuvants. Thus, Lockhoff et al. (U.S. Pat. No. 4,855,283 and ref. 60) reported that N-glycolipid analogs displaying structural similarities to the naturally-occurring glycolipids, such as glycosphingolipids and glycoglycerolipids, are capable of eliciting strong immune responses in both herpes simplex virus vaccine and pseudorabies virus vaccine. Some glycolipids have been synthesized from long chain alkylamines and fatty acids that are linked directly with the sugars through the anomeric carbon atom, to mimic the functions of the naturally occurring lipid residues.

U.S. Pat. No. 4,258,029 granted to Moloney, assigned to the assignee hereof and incorporated herein by reference thereto, teaches that octadecyl tyrosine hydrochloride (OTH) functions as an adjuvant when complexed with tetanus toxoid and formalin inactivated type I, II and III poliomyelitis virus vaccine. Also, Nixon-George et al. (ref. 61), reported that octodecyl esters of aromatic amino acids complexed with a recombinant hepatitis B surface antigen, enhanced the host immune responses against hepatitis B virus.

EXAMPLES

The above disclosure generally describes the present invention. A more complete understanding can be obtained by reference to the following specific Examples. These Examples are described solely for the purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Methods of protein biochemistry, fermentation and immunology used but not explicitly described in this disclosure and these Examples are amply reported in the scientific literature and are well within the ability of those skilled in the art.

Example 1

This Example describes the growth of *Bordetella pertussis*.

Master Seed:

Master seed cultures of a *Bordetella pertussis* strain were held as freeze-dried seed lots, at 2° C. to 8° C.

Working Seed:

The freeze-dried culture was recovered in Hornibrook medium and used to seed Bordet-Gengou Agar (BGA) plates. Hornibrook medium has the following composition:

| Component | for 1 liter |
| --- | --- |
| Casein hydrolysate (charcoal treated) | 10.0 g |
| Nicotinic acid | 0.001 g |
| Calcium chloride | 0.002 g |
| Sodium chloride | 5.0 g |
| Magnesium chloride hexahydrate | 0.025 g |
| Potassium chloride | 0.200 g |
| Potassium phosphate dibasic | 0.250 g |
| Starch | 1.0 g |
| Distilled water | to 1.0 liter |

The pH is adjusted to 6.9±0.1 with 1% sodium carbonate solution. The medium is dispensed into tubes and sterilized by steaming in the autoclave for 20 minutes and autoclaving for 20 minutes at 121° C. to 124° C. The seed was subcultured twice, firstly on BGA plates then on Component Pertussis Agar (CPA). Component Pertussis Agar (CPA) has the following composition:

| | |
| --- | --- |
| NaCl | 2.5 g/L |
| $KH_2PO_4$ | 0.5 g/L |
| KCl | 0.2 g/L |
| $MgCl_2 (H_2O)_6$ | 0.1 g/L |
| Tris base | 1.5 g/L |
| Casamino acids | 10.0 g/L |
| NaHGlutamate | 10.0 g/L |
| Conc. HCl | to pH 7.2 |
| Agar | 15.0 g/L |
| Growth factors (CPGF) | 10.0 mL/L |

Component Pertussis Growth Factors (CPGF)—100X have the following composition:

| | |
|---|---|
| L-cysteine HCl | 4.0 g/L |
| Niacin | 0.4 g/L |
| Ascorbic acid | 40.0 g/L |
| Glutathione, reduced | 15.0 g/L |
| $Fe_2SO_4$, $(H_2O)_7$ | 1.0 g/L |
| Dimethyl-β-cyclodextrin | 100 g/L |
| $CaCl_2$ $(H_2O)_2$ | 2.0 g/L |

The final culture was suspended in Pertussis Seed Suspension Buffer (CPSB), dispensed into 2 to 4 ml aliquots and stored frozen at −60° C. to −85° C. Pertussis Seed Suspension Buffer (PSSB) has the following composition:

| | |
|---|---|
| Casamino acids | 10.0 g/L |
| Tris base | 1.5 g/L |
| Anhydrous glycerol | 100 mL/L |
| Conc. HCl | to pH 7.2 |

These glycerol suspensions provided the starting material for the preparation of the working seed.

Cultivation Process:

Propagation of the working seed was conducted in Component Pertussis Agar Roux bottles for 4 to 7 days at 34° C. to 35° C. Following this cultivation, cells were washed off agar with Component Pertussis Broth (CPB). Samples were observed by Gram stain, for culture purity and opacity.

Cells were transferred to 4 liter conical flasks containing CPB and incubated at 34° C. to 38° C. for 20 to 26 hours with shaking. Samples were observed by Gram stain and culture purity was checked. Flasks were pooled and the suspension was used to seed two fermenters containing CPB (10 liter volume starting at $OD_{600}$ 0.1–0.4). The seed was grown to a final $OD_{600}$ of 5.0 to 10.0. Samples were tested by Gram strain, for culture purity, by antigen specific ELISAs and for sterility.

Example 2

This Example describes the purification of antigens from the *Bordetella pertussis* cell culture.

Production of Broth and Cell Concentrates:

Bacterial suspension was grown in two production fermenters, at 34° C. to 37° C. for 35 to 50 hours. The fermenters were sampled for media sterility testing. The suspension was fed to a continuous-flow disk-stack centrifuge (12,000×g) to separate cells from the broth. Cells were collected to await extraction of fimbriae component. The clarified liquor was passed through a 0.22 μm membrane filter. The filtered liquor was concentrated by ultra filtration using a 10 to 30 kDa nominal molecular weight limit (NMWL) membrane. The concentrate was stored to await separation and purification of the Pertussis Toxin (PT), Filamentous haemgglutonin (FHA) and 69 kDa (pertactin) components.

Separation of the Broth Components:

The broth components (69 kDa, PT and FHA) were separated and purified by perlite chromatography and selective elution steps, essentially as described in EP Patent No. 336 736 and applicants published PCT Application No. WO 91/15505, described above. The specific purification operations effected are described below.

Pertussis Toxin (PT):

The perlite column was washed with 50 mM Tris, 50 mM Tris/0.5% Triton X-100 and 50 mM Tris buffers. The PT fraction was eluted from the perlite column with 50 mM Tris/0.12M NaCl buffer.

The PT fraction from the perlite chromatography was loaded onto a hydroxylapatite column and then washed with 30 mM potassium phosphate buffer. PT was eluted with 75 mM potassium phosphate/225 mM NaCl buffer. The column was washed with 200 mM potassium phosphate/0.6M NaCl to obtain the FHA fraction which was discarded. Glycerol was added to the purified PT to 50% and the mixture was stored at 2° C. to 8° C. until detoxification, within one week.

Filamentous Haemagglutonin (FHA):

The FHA fraction was eluted from the perlite column with 50 mM Tris/0.6M NaCl. Filamentous haemagglutinin was purified by chromatography over hydroxylapatite. The FHA fraction from the perlite column was loaded onto a hydroxylapatite column then washed with 30 mM potassium phosphate containing 0.5% Triton X-100, followed by 30 mM potassium phosphate buffer. The PT fraction was eluted with 85 mM potassium phosphate buffer and discarded. The FHA fraction was then eluted with 200 mM potassium phosphate/0.6M NaCl and stored at 2° C. to 8° C. until detoxification within one week.

69 kDa (pertactin):

The broth concentrate was diluted with water for injection (WFI) to achieve a conductivity of 3 to 4 mS/cm and loaded onto a perlite column at a loading of 0.5 to 3.5 mg protein per ml perlite. The run-through (69 kDa Component Fraction) was concentrated by ultrafiltration using a 10 to 30 kDa NMWL membrane. Ammonium sulphate was added to the run-through concentrate to 35%±3% (w/v) ammonium sulphate precipitation of concentrated perlite run-through was used for the purification. Ammonium sulphate (100±5 g per liter) was added to the 69 kDa fraction and the mixture stirred for at least 2 hours at 2° C. to 8° C. The mixture was centrifuged (7,000×g) to recover the pellet, which was dissolved in 10 mM Tris, HCl, pH 8. The ionic strength of the solution was adjusted to the equivalent of 10 mM Tris HCl (pH 8), containing 15 mM ammonium sulphate.

The 69 kDa protein was applied to a hydroxylapatite column connected in tandem with a Q-Sepharose column. The 69 kDa protein was collected in the run-through, was flushed from the columns with 10 mM Tris, HCl (pH 8), containing 15 mM ammonium sulphate and pooled with 69 kDa protein in the run-through. The 69 kDa protein pool was diafiltered with 6 to 10 volumes of 10 mM potassium kDa NMWL membrane. The ultra filtrate was collected and the 69 kDa protein in the ultra filtrate concentrated.

The 69 kDa protein was solvent exchanged into 10 mM Tris HCl (pH8), and adsorbed onto Q-Sepharose, washed with 10 mM Tris HCl (pH 8)/5 mM ammonium sulphate. The 69 kDa protein was eluted with 50 mM potassium phosphate (pH 8). The 69 kDa protein was diafiltered with 6 to 10 volumes of 10 mM potassium phosphate (pH 8) containing 0.15M NaCl on a 10 to 30 kDa NMWL membrane. The 69 kDa protein was sterile filtered through a ≦0.22 μm filter. This sterile bulk was stored at 2° C. to 8° C. and adsorption was performed within three months.

Fimbrial Agglutinogens:

The agglutinogens were purified from the cell paste following separation from the broth. The cell paste was diluted to a 0.05 volume fraction of cells in a buffer containing 10 mM potassium phosphate, 150 mM NaCl and 4M urea and was mixed for 30 minutes. The cell lysate was clarified by centrifugation (12,000×g) then concentrated and diafiltered against 10 mM potassium phosphate/150 mM NaCl/0.1% Triton X-100 using a 100 to 300 kDa NMWL membrane filter.

The concentrate was heat treated at 80° C. for 30 min then reclarified by centrifugation (9,000×g). PEG 8000 was added to the clarified supernatant to a final concentration of 4.5%±0.2% and stirred gently for a minimum of 30 minutes. The resulting precipitate was collected by centrifugation (17,000×g) and the pellet extracted with 10 mM potassium phosphate/150 mM NaCl buffer to provide a crude fimbrial agglutinogen solution. The fimbrial agglutinogens were purified by passage over PEI silica. The crude solution was made 100 mM with respect to potassium phosphate using 1M potassium phosphate buffer and passed through the PEI silica column.

The run-through from the columns was concentrated and diafiltered against 10 mM potassium phosphate/150 mM NaCl buffer using a 100 to 300 kDa NMWL membrane filter. This sterile bulk is stored at 2° C. to 8° C. and adsorption performed within three months. The fimbrial agglutinogen preparation contained fimbrial Agg 2 and fimbrial Agg 3 in a weight ratio of about 1.5 to about 2:1 and was found to be substantially free from Agg 1.

Example 3

This Example describes the toxoiding of the purified *Bordetella pertussis* antigens, PT and FHA.

PT, prepared in pure form as described in Example 2, was toxoided by adjusting the glutaraldehyde concentration in the PT solution to 0.5%±0.1% and incubating at 37° C.±3° C. for 4 hours. The reaction was stopped by adding L-aspartate to 0.21±0.02M. The mixture was then held at room temperature for 1±0.1 hours and then at 2° C. to 8° C. for 1 to 7 days.

The resulting mixture was diafiltered against 10 mM potassium phosphate/0.15M NaCl/5% glycerol buffer on a 30 kDa NMWL membrane filter and then sterilized by passage through a ≦0.22 μm membrane filter. This sterile bulk was stored at 2° C. to 8° C. and adsorption performed within three months.

The FHA fraction, prepared in pure form as described in Example 2, was toxoided by adjusting the L-lysine and formaldehyde concentration to 47±5 mM and 0.4±0.05% respectively and incubating at 35° C. to 38° C. for 6 weeks. The mixture was then diafiltered against 10 mM potassium phosphate/0.5M NaCl using a 30 kDa NMWL membrane filter and sterilized by passage through a membrane filter. This sterile bulk was stored a 2° C. to 8° C. and adsorption performed within three months.

Example 4

This Example describes the adsorption of the purified *Bordetella pertussis* antigens.

For the individual adsorption of PT, FHA, Agg and 69 kDa onto aluminum phosphate (alum), a stock solution of aluminum phosphate was prepared to a concentration of 18.75±1 mg/ml. A suitable vessel was prepared and any one of the antigens aseptically dispensed into the vessel. 2-phenoxyethanol was aseptically added to yield a final concentration of 0.6%±0.2% v/v and stirred until homogeneous. The appropriate volume of aluminum phosphate was aseptically added into the vessel. An appropriate volume of sterile distilled water was added to bring the final concentration to 3 mg aluminum phosphate/ml. Containers were sealed and labelled and allowed to stir at room temperature for 4 days. The vessel was then stored awaiting final formulation.

Example 5

This Example describes the formulation of a component pertussis vaccine combined with diphtheria and tetanus toxoids.

The *B. pertussis* antigens prepared as described in the preceding Examples were formulated with diphtheria and tetanus toxoids to provide several component pertussis (CP) vaccines.

The pertussis components were produced from *Bordetella pertussis* grown in submerged culture as described in detail in Examples 1 to 4 above. After completion of growth, the culture broth and the bacterial cells were separated by centrifugation. Each antigen was purified individually. Pertussis toxin (PT) and Filamentous Haemagglutinin (FHA) were purified from the broth by sequential chromatography over perlite and hydroxylapatite. PT was detoxified with glutaraldehyde and any residual PT (approximately 1%) present in the FHA fraction was detoxified with formaldehyde. Fimbrial Agglutinogens (2÷3) (AGG) were prepared from the bacterial cells. The cells were disrupted with urea and heat treated, and the fimbrial agglutinogens were purified by precipitation with polyethylene glycol and chromatography over polyethyleneimine silica. The 69 kDa protein (pertactin) component was isolated from the run through from the perlite chromatography step (Example 2) by ammonium sulphate precipitation, and purified by sequential chromatography over hydroxylapatite and Q-sepharose. All components were sterilized by filtration through a 0.22 μm membrane filter.

Diphtheria toxoid was prepared from *Corynebacterium diphtheriae* grown in submerged culture by standard methods. The production of Diphtheria Toxoid is divided into five stages, namely maintenance of the working seed, growth of *Corynebacterium diphtheriae*, harvest of Diphtheria Toxin, detoxification of Diphtheria Toxin and concentration of Diphtheria Toxoid.

Preparation of Diphtheria Toxoid (I) Working Seed

The strain of *Corynebacterium diphtheriae* was maintained as a freeze-dried seed lot. The reconstituted seed was grown on Loeffler slopes for 18 to 24 hours at 35° C.±2° C., and then transferred to flasks of diphtheria medium. The culture was then tested for purity and Lf content. The remaining seed was used to inoculate a fermenter.

(II) Growth of *Corynebacterium diphtheriae*

The culture was incubated at 35° C.±2° C. and agitated in the fermenter. Predetermined amounts of ferrous sulphate, calcium chloride and phosphate solutions were added to the culture. The actual amounts of each solution (phosphate, ferrous sulphate, calcium chloride) were determined experimentally for each lot of medium. The levels chosen are those which gave the highest Lf content. At the end of the growth cycle (30 to 50 hours), the cultures were sampled for purity, and Lf content.

The pH was adjusted with sodium bicarbonate, and the culture inactivated with 0.4% toluene for 1 hour at a maintained temperature of 35° C.±2° C. A sterility test was then performed to confirm the absence of live *C. diphtheriae.*

(III) Harvest of Diphtheria Toxin

The toluene treated cultures from one or several fermenters were pooled into a large tank. Approximately 0.12% sodium bicarbonate, 0.25% charcoal, and 23% ammonium sulphate were added, and the pH was tested.

The mixture was stirred for about 30 minutes. Diatomaceous earth was added and the mixture pumped into a depth filter. The filtrate was recirculated until clear, then collected, and sampled for Lf content testing. Additional ammonium sulphate was added to the filtrate to give a concentration of 40%. Diatomaceous earth was also added. This mixture was held for 3 to 4 days at 2° C. to 8° C. to allow the precipitate to settle. Precipitated toxin was collected and dissolved in 0.9% saline. The diatomaceous earth was removed by filtration and the toxin dialysed against 0.9% saline, to remove the ammonium sulphate. Dialysed toxin was pooled and sampled for Lf content and purity testing.

(IV) Detoxification of Diphtheria Toxin

Detoxification takes place immediately following dialysis. For detoxification, the toxin was diluted so that the final solution contained:

a) diphtheria toxin at 1000±10% Lf/ml.
b) 0.5% sodium bicarbonate
c) 0.5% formalin
d) 0.9% w/v L-lysine monohydrochloride The solution was brought up to volume with saline and the pH adjusted to 7.6±0.1.

Toxoid was filtered through cellulose diatomaceous earth filter pads and/or a membrane prefilter and 0.2 µm membrane filter into the collection vessel and incubated for 5 to 7 weeks at 34° C. A sample was withdrawn for toxicity testing.

(V) Concentration of Purified Toxoid

The toxoids were pooled, then concentrated by ultrafiltration, and collected into a suitable container. Samples were taken for Lf content and purity testing. The preservative (2-phenoxyethanol) was added to give a final concentration of 0.375% and the pH adjusted to 6.6 to 7.6.

The toxoid as sterilized by filtration through a prefilter and a 0.2 µm membrane filter (or equivalent) and collected. The sterile toxoid was then sampled for irreversibility of toxoid Lf content, preservative content, purity (nitrogen content), sterility and toxicity testing. The sterile concentrated toxoid was stored at 2° C. to 8° C. until final formulation.

Preparation of Tetanus Toxoid

Tetanus toxoid (T) was prepared from *Clostridium tetani* grown in submerged culture.

The production of Tetanus Toxoid can be divided into five stages, namely maintenance of the working seed, growth of *Clostridium tetani*, harvest of Tetanus Toxin, detoxification of Tetanus Toxin and purification of Tetanus Toxoid.

(I) Working Seed

The strain of *Clostridium tetani* used in the production of tetanus toxin for the conversion to tetanus toxoid was maintained in the lyophilized form in a seed-lot. The seed was inoculated into thioglycollate medium and allowed to grow for approximately 24 hours at 35° C.±2° C. A sample was taken for culture purity testing.

(II) Growth of *Clostridium tetani*

The tetanus medium was dispensed into a fermenter, heat-treated and cooled. The fermenter was then seeded and the culture allowed to grow for 4 to 9 days at 34° C.±2° C. A sample was taken for culture purity, and Lf content testing.

(III) Harvest of Tetanus Toxin

The toxin was separated by filtration through cellulose diatomaceous earth pads, and the clarified toxin then filter-sterilized using membrane filters. Samples were taken for Lf content and sterility testing. The toxin was concentrated by ultrafiltration, using a pore size of 30,000 daltons.

(IV) Detoxification of Tetanus Toxin

The toxin was sampled for Lf content testing prior to detoxification. The concentrated toxin (475 to 525 Lf/ml) was detoxified by the addition of 0.5% w/v sodium bicarbonate, 0.3% v/v formalin and 0.9% w/v L-lysine monohydrochloride and brought up to volume with saline. The pH was adjusted to 7.5±0.1 and the mixture incubated at 37° C. for 20 to 30 days. Samples were taken for sterility and toxicity testing.

(V) Purification of Toxoid

The concentrated toxoid was sterilized through prefilters, followed by 0.2 µm membrane filters. Samples were taken for sterility and Lf content testing.

The optimum concentration of ammonium sulphate was based on a fractionation "S" curve determined from samples of the toxoid. The first concentration was added to the toxoid (diluted to 1900–2100 Lf/ml). The mixture was kept for at least 1 hour at 20° C. to 25° C. and the supernatant collected and the precipitate containing the high molecular weight fraction, discarded.

A second concentration of ammonium sulphate was added to the supernatant for the second fractionation to remove the low molecular weight impurities. The mixture was kept for at least 2 hours at 20° C. to 25° C. and then could be held at 2° C. to 8° C. for a maximum of three days. The precipitate, which represents the purified toxoid, was collected by centrifugation and filtration.

Ammonium sulphate was removed from the purified toxoid by diafiltration, using Amicon (or equivalent) ultrafiltration membranes with PBS until no more ammonium sulphate could be detected in the toxoid solution. The pH was adjusted to 6.6. to 7.6, and 2-phenoxyethanol added to give a final concentration of 0.375%. The toxoid was sterilized by membrane filtration, and samples are taken for testing (irreversibility of toxoid, Lf content, pH, preservative content, purity, sterility and toxicity).

One formulation of a component pertussis vaccine combined with diphtheria and tetanus toxoids was termed $CP_{10/5/5/3}DT$. Each 0.5 ml human dose of $CP_{10/5/5/3}DT$ was formulated to contain:

| | |
|---|---|
| 10 µg | Pertussis toxoid (PT) |
| 5 µg | Filamentous haemagglutonin (FHA) |
| 5 µg | Fimbrial agglutinogens 2 and 3 (FIMB) |
| 3 µg | 69 kDa outer membrane protein |
| 15 Lf | Diphtheria toxoid |
| 5 Lf | Tetanus toxoid |
| 1.5 mg | Aluminum phosphate |
| 0.6% | 2-phenoxyethanol as preservative |

Another formulation of component pertussis vaccine combined with diphtheria and tetanus toxoids was termed $CP_{10/5/5}DT$. Each 0.5 ml human dose of $CP_{10/5/5}DT$ was formulated to contain:

| | |
|---|---|
| 10 µg | Pertussis toxoid (PT) |
| 5 µg | Filamentous haemagglutonin (FHA) |
| 5 µg | Fimbrial agglutinogens 2 and 3 (FIMB) |
| 15 Lf | Diphtheria toxoid |
| 5 Lf | Tetanus toxoid |
| 1.5 mg | Aluminum phosphate |
| 0.6% | 2-phenoxyethanol as preservative |

Another formulation of Component Pertussis vaccine combined with diphtheria and tetanus toxoids was termed $CP_{20/20/5/3}DT$. Each 0.5 ml human dose of $CP_{20/20/5/3}DT$ was formulated to contain:

| | |
|---|---|
| 20 µg | Pertussis toxoid (PT) |
| 20 µg | Filamentous haemagglutonin (FHA) |
| 5 µg | Fimbrial agglutinogens 2 and 3 (FIMB) |
| 3 µg | 69 kDa outer membrane protein |
| 15 Lf | Diphtheria toxoid |
| 5 Lf | Tetanus toxoid |
| 1.5 mg | Aluminum phosphate |
| 0.6% | 2-phenoxyethanol as preservative |

A further formulation of a component pertussis vaccine combined with diphtheria and tetanus toxoids was termed $CP_{20/10/10/5}DT$. Each 0.5 ml human dose of $CP_{20/10/10/5}DT$ was formulated to contain:

| | |
|---|---|
| 20 µg | Pertussis toxoid (PT) |
| 10 µg | Filamentous haemagglutonin (FHA) |
| 10 µg | Fimbrial agglutinogens 2 and 3 (FIMB) |
| 6 µg | 69 kDa outer membrane protein |
| 15 Lf | Diphtheria toxoid |
| 5 Lf | Tetanus toxoid |
| 1.5 mg | Aluminum phosphate |
| 0.6% | 2-phenoxyethanol as preservative |

Example 6

This Example describes the clinical assessment of Component Acellular Pertussis vaccines, produced in accordance with the invention.

(a) Studies in Adults

Studies in adults and children aged 16 to 20 months indicated the multi-component vaccines containing fimbrial agglutinogens to be safe and immunogenic (Table 2).

A Phase I clinical study was performed in 17 and 18 month old children in Calgary, Alberta with the five Component Pertussis vaccine ($CP_{10/5/5/3}DT$) and the adverse reaction reported. Thirty-three children received the vaccine and additionally 35 received the same vaccine without the 69 kDa protein component.

Local reactions were rare. Systemic adverse reactions, primarily consisting of irritability were present in approximately half of study participants, regardless of which vaccine was given. Significant antibody rises were measured for anti-FT, anti-FHA, anti-fimbrial agglutinogens and anti-69 kDa IgG antibodies by enzyme immunoassay and anti-PT antibodies in the CHO cell neutralization test. No differences in antibodies response were detected in children who received the four component ($CP_{10/5/5}DT$) or five component ($CP_{10/5/5/3}DT$) except in the anti-69 kDa antibody. Children who received the five component vaccine containing the 69 kDa protein had a significantly higher post-immunization anti-69 kDa antibody level.

A dose-response study was undertaken with the 4 component vaccine in Winnipeg, Manitoba, Canada. Two component vaccine formulations were used: $CP_{10/5/5/3}DT$ and $CP_{20/10/10/6}DT$. A whole-cell DPT vaccine was also included as a control.

This study was a double-blind study in 91, 17 to 18 month old infants at the time of their booster pertussis dose. Both $CP_{10/5/5/3}DT$ and $CP_{20/20/10/6}DT$ were well tolerated by these children. No differences were demonstrated in the number of children who had any local reaction, or systemic reactions after either of the component vaccines. In contrast, significantly more children who received the whole-cell vaccine had local and systemic reactions than those who received the $CP_{20/10/10/6}DT$ component vaccines.

Studies in Infants:

Phase II:

A study was conducted using the $CP_{10/5/5/3}DT$ vaccine in Calgary, Alberta and British Columbia, Canada. In this study, 432 infants received the component pertussis vaccine or the whole-cell control vaccine DPT at 2, 4 and 6 months of age. The $CP_{10/5/5/3}DT$ vaccine was well tolerated by these infants. Local reactions were less common with the component vaccine than the whole cell vaccine after each dose.

A significant antibody response to all antigens was demonstrated after vaccination with the component pertussis vaccine. Recipients of the whole-cell vaccine had a vigorous antibody response to fimbrial agglutinogens, D and T. At seven months, 82% to 89% of component vaccine recipients and 92% of whole cell vaccine recipients had a four-fold increase or greater rise in antibody titer to fimbrial agglutinogens. In contrast, antibody response to FHA was 75% to 78% in component vaccines compared to 31% of whole-cell recipients. A four-fold increase in anti-69 kDa antibody was seen in 90% to 93% of component vaccines and 75% of whole-cell recipients. A four-fold rise in antibody against PT by enzyme immunoassay was seen in 40% to 49% of component vaccines and 32% of whole-cell vaccines; a four-fold rise in PT antibody by CHO neutralization was found in 55% to 69% of component and 6% of whole-cell vaccines. (Table 2).

Phase IIB:

The $CP_{20/20/5/3}DT$ and $CP_{10/10/5/3}DT$ vaccines were assessed in a randomized blinded study against a $D_{15}DT$ control with a lower diphtheria content of 15 Lf compared to a 25 Lf formulation of 100 infants at 2, 4 and 6 months of age. No differences in rates of adverse reactions were detected between the two components formulations; both were significantly less reactogenic than the whole-cell control. Higher antibody titers against PT by enzyme immunoassay and CHO neutralization and FHA were achieved in recipients of the $CP_{20/20/5/3}DT$ vaccine with increased antigen content. At 7 months, the anti-FHA geometric mean titer was 95.0 in $CP_{20/20/5/3}DT$ recipients, 45.2 in $CP_{10/5/5/3}DT$ recipients were only 8.9 in $D_{15}DT$ recipients. Anti-PT titers were 133.3, 58.4 and 10.4 by immunoassay and 82.4, 32.7 and 4.0 by CHO neutralization respectively (Table 2).

This study demonstrated that the Component Pertussis vaccine combined with diphtheria and tetanus toxoids adsorbed, with increased antigen content, was safe and immunogenic in infants and that the increased antigen content augmented the immune response to the prepared antigens (PT and FHA) without an increase in reactogenicity.

NIAID, PHASE II, U.S. Comparative Trial:

A phase II study was performed in the United States under the auspices of the National Institute of Allergy and Infectious Diseases (NIAID) as a prelude to a large scale efficacy trial of acellular pertussis vaccines. One component pertussis vaccine of the invention in combination with diphtheria and tetanus toxoids adsorbed ($CP_{10/5/5/3}DT$) was included in that trial along with 12 other acellular vaccines and 2 whole-cell vaccines. Safety results were reported on 137 children immunized at 2, 4 and 6 months of age with the $CP_{10/5/5/3}DT$ component vaccine.

As seen in previous studies, the component vaccine was found to be safe, of low reactogenicity and to be well tolerated by vaccines.

At 7 months, anti-PT antibody, anti-FHA antibody, anti-69 kDa antibody and anti-fimbrial agglutinogens antibody were all higher than or equivalent to levels achieved after the whole-cell vaccines (ref 71 and Table 2). A double blind study was performed in which children were randomly allocated to receive either the $CP_{20/20/5/3}DT$ or the $CP_{10/5/5/3}DT$ vaccine formulation. A total of 2050 infants were enrolled in the United States and Canada; 1961 infants completed the study. Both vaccine formulations were safe, and low reactogenicity and immunogenic in these infants. Immunogenicity was assessed in a subgroup of 292. An antibody rise was elicited to all antigens contained in the vaccine by both vaccine formulations. The $CP_{20/20/5/3}DT$ formulation induced higher antibody titers against FHA but not PT. The $CP_{10/5/5/3}DT$ formulation elicited higher titers against fimbriae and higher agglutinogen titers.

A further safety and immunogenicity study was conducted in France. The study design was similar to the North American study, described above, except that vaccines were administered at 2, 3 and 4 months of age. Local and systemic reactions were generally minor. Overall the vaccine was well accepted by the French study participants using this administration regime.

Placebo-controlled efficacy trial of two acellular pertussis vaccines and of a whole-cell vaccine in 10,000 infants Following the results of the NIAID Phase II U.S. comparative trial, a two-component and a five-component acellular vaccine were selected for a multi-centre, controlled, double-randomized placebo-controlled efficacy trial. The clinical trial was performed in Sweden, where there is a high incidence of pertussis. The two-component vaccine contained glyceraldehyde and formalin inactivated PT (25 μg), formalin treated FHA (25 μg) and diphtheria toxoid 17 Lf and tetanus toxoid 10 Lf. The five-component pertussis vaccine was $CP_{10/5/5/3}DT$. For the trial, ten thousand infants, representing approximately one-half the infants of this age group in Sweden, were recruited in 14 geographically defined study sites by use of birth registry.

Children born in January and February 1992 were randomized into a 3-armed trial. After parental consent, two-thirds of the infants received one out of the two diphtheria-tetanus-acellular pertussis preparations at two, four and six months of age. The control group received DT only. In May 1992, a U.S. Licensed commercially-available whole-cell DTP vaccine was introduced and children born in March through December 1992 were randomized into a 4-armed trial. After parental consent, three-quarters of the infants received one out of three DTP preparations at two, four and six months of age. The control group received DT only.

Each vaccine was administered to about 2,500 children. Vaccines were administered in three doses. The first dose was given at 2 months of age and not later than 3 months of age. Subsequent doses were given with 8 week intervals. Vaccines were given by intramuscular injection.

The children and their households were followed for 30 months. If pertussis was suspected, clinical data was collected, and laboratory verification sought by nasal aspirates for bacteriological culture and polymerase chain reaction (PCR) diagnosis. Acute and convalescent blood samples were collected for serological diagnosis.

Prior to this study, the extent of pertactin afforded by component pertussis vaccines of the present invention in an at-risk human population (particularly neonates) was unknown. In particular, the contribution of the various Bordetella components and their presence in pertussis vaccines in selected relative amounts to efficacy of the vaccines was not known.

The main aim of the trial was to estimate the ability of acellular pertussis vaccines and whole-cell vaccine to protect against typical pertussis as compared to placebo.

A secondary end-point was to explore vaccine efficacy against confirmed pertussis infection of varying severity.

Vaccine efficacy is defined as the per cent reduction in the probability of contracting pertussis among vaccine recipients relative to unvaccinated children.

The relative risk of pertussis in two vaccine groups is expressed as the ratio of the disease probability in the two groups.

The probability of contracting pertussis, also called the attack rate, can be estimated in different ways. In the calculations of the sample size, the probability of contracting pertussis in a given study group is estimated by the quotient between the number of children with pertussis and the children remaining in the study group at the termination of study follow-up.

The efficacy of the component vaccine $CP_{10/5/5/3}DT$ in this trial in preventing typical pertussis is shown in Table 4 and was about 85%. In the same trial, a two-component pertussis acellular vaccine containing only PT and FHA was about 58% efficacious and a whole-cell vaccine was about 48% efficacious. The $CP_{10/5/5/3}DT$ was also effective in preventing mild pertussis at an estimated efficacy of about 77%.

Example 7

This Example describes the formulation and immunogenicity of multi-valent combination vaccine containing a capsular polysaccharide of *Haemophilus influenzae*.

The capsular polysaccharide (PRP) from *H. influenzae* was purified and conjugated to tetanus toxoid in the following manner. From lyophilized ampules of working seed lot of *H. influenzae*, three successive precultures are performed. The first preculture is on solid medium. Ampules are inoculated onto dishes of charcoal agar+boiled blood (10% of horse blood heated for 15 min at 80° C.) and incubated for 20±4 hours at 36° C.–37° C. under $CO_2$. The second preculture is in liquid medium for 8 hours at 37° C. The liquid medium had the following composition per liter:

| 1. | Casamino-acids Difco | 10 g |
|---|---|---|
| | Monosodium phosphate $2H_2O$ | 2.03 g |
| | Disodium phosphate $12H_2O$ | 31.14 g |
| | Sodium lactate (60% solution) | 1.5 ml |
| | L-cystine | 0.07 g |
| | L-tryptophans | 0.02 g |
| | $CaCL_2, 2H_2O$ | 0.02 g |
| | $(NH4)_2SO_4$ | 1 g |
| | $MgSO_4, 7H_2O$ | 0.4 g |
| | Antifoam Dow Corning M.S.A At 25% in paraffin oil | 0.15 ml |

2. Ultrafiltrate of hemine+dextrose at the proportion of 20 g dextrose and 1 mg hemine. This solution is added with 5 mg of nicotinamide-adenine dinulceotide Filter sterilized.

3. Yeast extract Difco 5 g Filter sterilized.

The third preculture is in liquid medium with stirring for 4 hours at 37° C. The third preculture is used to inoculate the fermenter and the culture is maintained with stirring, at 37° C. for 12 to 14 hours. The culture is collected in a refrigerated tank. Formalin is added at a concentration of 10 ml/liter. The culture is maintained, with gentle stirring, at +4° C. for 2–24 hours and then centrifuged. The formalin added is not intended to completely inactivate the bacteria but to arrest growth and inhibit metabolism. This addition reduces cell lysis with consequent contamination with intracellular components. The duration of this fixation is between 2 and 24 hours and typically the culture is left overnight before being centrifuged. The supernatant containing the polysaccharide is harvested and the bacterial pellet is discarded. The purification process is generally performed in a cold room or in conditions such that the temperature of products and reagents is less than or equal to +10° C. except for the phenol purification step which is carried out at room temperature. After centrifugation of the culture, the supernatant of the culture is concentrated. The capsular polysaccharide is precipitated from the resulting concentrate by addition of centrimide to give a final concentration of 5% W/V. Centrimide precipitates PS from the concentrated fluid (SNF). Some protein, nucleic acid and lipopolysaccharide (LPS) are also co-precipitated. The precipitates are collected by centrifugation leaving some other contaminants and protein behind in the SNF. The resulting pellet is collected by centrifugation and stored at $\leq-20°$ C.

The pellets were resuspended in 0.3 M NaCl solution and the suspension centrifuged again. NaCl selectively dissociates polysaccharide centrimide complexes. Some contaminants (nucleic acid, LPS, protein) are also dissociated in the process. To the supernate precooled absolute ethanol up to a final concentration of 60% is added. The resulting precipitate is collected by centrifugation and washed with cold, absolute ethanol. The precipitate is dried under vacuum at 0–4° C., and is the intermediate product. The intermediate product is dissolved in sodium acetate buffer and with phenol at room temperature. The aqueous phase was collected by continuous centrifugation. The phenol extraction and centrifugation may be repeated several times and the aqueous phase was dialysed and diafiltered. The capsular polysaccharide from the diafiltered solution was precipitated by addition of precooled ethanol up to a final concentration of 60% in the presence of NaCl 0.3 M. The precipitate was collected by centrifugation, washed with precooled absolute ethanol, acetone and ether and dried under vacuum at 4° C. The dried precipitate was then ground to a fine powder under low humidity and this constitutes the purified *Haemophilus influenzae* type b polysaccharide.

The purified polysaccharide was dissolved in water in order to obtain 5 mg polysaccharide per ml solution, and the pH adjusted to 10.8±0.2 with NaOH. Cyanogen bromide as a solution in water was added in the proportions of 0.5 mg CNBr/mg polysaccharide. The pH of the reaction mixture was maintained with NaOH at 10.8±0.2 for 35 to 40 minutes at 23°±3° C. The pH was lowered to pH9 by the addition of HCl. Adapic acid dihydrazide was added to give a final concentration of 3.5 mg ADH/mg polysaccharide and the pH adjusted to 8.5. The reaction mixture was incubated at 23±3° C. for 15 minutes (pH maintained at 8.5) and then the solution was incubated overnight at +4° C., with gentle stirring. The reaction mixture was dialyzed against NaCl solution and then concentrated. The solution was then filtered through a 0.45μ filter and frozen at $\leq-40°$ C. This constitutes the AH-polysaccharide and was stored at a temperature $\leq-40°$ C.

To produce the tetanus toxin component, a strain of *Clostridium tetani* was inoculated into a series of tubes containing 10 ml of Rosenow medium or thioglycolate medium. Rosenow medium has the following composition:

| | |
|---|---|
| Peptone | 10 |
| Meat extract | 3 |
| Glucose | 2 |
| Sodium chloride | 5 |
| "Andrade"s indicator (5% Fuchsin acid) | 10 ml |
| White marble | 1 piece |
| Brain | 1 piece |

The medium, prepared immediately prior to use from ready for use products, is filled into tubes and sterilized at 120° C. for 20 minutes.

A 5 liter bottle containing 3 liters of "Massachusetts" medium was inoculated with *C. tetani* and incubated for 16 to 18 hours at 35° C.±1° C. for 16 hours. The contents were then transferred to a 20 liter bottle containing 15 liters of sterile "Maassachusetts" medium and incubated 8 hours at 35°C.±1° C. Each bottle was used to inoculate a fermenter containing 582 liters of "Massachusetts" medium and incubated at 35° C. for 5 to 6 days with aeration. The fermenters were cooled and to the culture was added sodium chloride 12 kg, trisodium citrate 8 kg. Shaking was maintained for one day then stopped and this process allows extraction of the residual toxin from the bacteria at the end of the culture. The toxin was clarified either by filtration or by passage through a continuous centrifuge.

The supernatant from 1200 l of culture was concentrated by ultra filtration and the concentrated toxin diafiltered against 0.07 M disodium phosphate solution pH 8.2. The final volume was adjusted to 500 Lf/m.

A double precipitation with ammonium sulphate was performed to obtain the purified tetanus toxin. Thus, ammonium sulphate and 10 g of charcoal are slowly added per liter of the previously obtained diafiltered toxin. After 16 to 24 hours incubation at +4° C., the toxin was filtered on cartridges to eliminate the precipitate. Then, a quantity of ammonium sulphate sufficient to make 320 gm/L were slowly added per liter of the previously obtained supernatant. After about 48 hours at +4° C. the pellet was collected by centrifugation and dissolved in a 0.05 M disodium phosphate solution pH 8.2. The solution was diafiltered against 0.05 M disodium phosphate solution pH 8.2 and adjusted to 300 Lf/ml. The solution was then filter sterilized. 7.5 μ moles (0.225%) of formaldehyde were added per ml of the toxin solution. Detoxification is achieved after incubation for 24 days at +37° C. including intermediate periods at +4° C. and +22° C. Sterilization by filtration (0.22 μ) is performed to obtain the tetanus toxoid. The tetanus toxoid is dialyzed and concentrated against NaCl using a membrane having a cut off of molecular weight $\leq 50,000$. The concentration protein is then aseptically filtered and stored at +4° C.

Equal amounts of AH— polysaccharide and tetanus toxoid (±20%) were mixed with 0.05 M NaCl to give a concentration of 7.5 mg polysaccharide per ml. The pH of the solution was adjusted to pH 5.7+0.2 with HCl and 1-ethyl 3-(3 dimethyl aminopropyl) carbodiimide (EDAC) added to give a final concentration of 19.17 mg EDAC/ml of reaction mixture. The carboxyl groups of the tetanus protein are activated by binding to EDAC. Under the slightly acid conditions of the reaction, there follows a condensation reaction in which the AH-PS and the EDAC-activated tetanus protein become covalently bound. The mixture was incubated at constant pH (5.7) for 60 minutes at +4° C., and then the pH adjusted to pH 6.9±0.2 with NaOH and the reaction mixture dialyzed against NaCl at +4° C. The conjugate is purified by zonal centrifugation on a sucrose gradient (4% to 60%) to eliminate EDAC, free AH-polysaccharide, free tetanus protein, and low molecular weight conjugate. To the fraction containing the polysaccharide conjugate. To the fraction containing the polysaccharide conjugate was then added pyrogen free water, sucrose, Tris-HCl buffer to obtain a conjugate solution of the following composition:

sucrose 8.5% W/V±0.5% polysaccharide conc. approximately 200 µg/ml

Tris-HCl buffer 10 mM pH 7.0±0.5.

The solution was then aseptically filtered using a 0.2 µ filter and stored at −40° C.

The *Haemophilus influenzae* type b polysaccharide conjugate bulk was diluted under sterile conditions with diluent in order to obtain the final composition:

| Polysaccharide Haemophilus type b conjugate concentrated bulk | to | 200 mg of polysaccharide |
|---|---|---|
| Tris-MCl buffer 200 mM to pH 7.2 | to | 10 mM |
| Sucrose | to | 850 g |
| Water for injection | to | 10 l |

The final bulk is filled into vials and lyophilized. (The lyophilized vaccine is reconstituted with 0.5 ml or 0.4% NaCl for use).

Two formulations of APDT were analyzed. The first (APDT-low) contained 10 µg pertussis toxoid (PT), 5 µg filamentous hemagglutinin (FHA), 5 µg fimbriae 2 and 3 µg 69 K protein (69K) per 0.5 ml dose (CLASSIC). The second formulation (APDT-high) contained twice the quantity of PT (20 µg) and identical amounts of FIM and 69K (HYBRID). Both formulations contained 15 Limit of flocculation (Lf) diphtheria toxoid, 5 Lf tetanus toxoid, 1.5 mg aluminum phosphate as adjuvant and 0.6% 2-phenoxyethanol as preservative. The Hib-tetanus toxoid conjugate vaccine (PRPT) was produced by Connaught Laboratories Inc. (Swiftwater, U.S.A.)

Population

Healthy 17 to 21 month old children who had been immunized with three doses of either APDT-low or PRPT as separate injections at 2, 4, and 6 months of age in a previous clinical trial [28] were recruited into the study. Following written informed consent, children were allocated by a computer-generated balanced block list of random numbers to receive PRT either as a separate injection on the same day, s a separate injection with the PRPT given one month after the APDT vaccine, or as a single injection (lyophilized PRPT reconstituted in APDT). The APDT formulation (high or low) for each child remained the same as had been given for the first three doses (allocation ratio 6:1 APDT-high; APDT-low). Vaccines were given i.m. with a 25 mm needle into the deltoid muscle of the arm or the vastus lateralis muscle of the thigh if the deltoid was of insufficient mass. Where a second injection was required for PRPT, the opposite limb was injected.

Clinical and Laboratory Monitoring

Participants were monitored for local and systemic adverse reactions immediately following the immunization and by the parents for 72 hours post-immunization. Data were collected via a structure telephone interview at 24 and 72 hours. Body temperature was measured at least once daily or whenever the child was thought by parents to be febrile. Tenderness and systemic reactions (irritability, decreased activity, decreased feeding) were graded as mild, moderate, or sever according to pre-established criteria by which the parent selected a severity based on structured examples. Measured local reactions were graded by their size and prolonged crying by its duration.

Blood samples were collected by venipuncture or by finger-prick prior to and 28 days after immunization; in children given the PRPT injection (therefore, 2 months post-APDT). Antibodies to the capsular polysaccharide of Hib (PRP) were measured by RIA. IgG antibodies to PT were measured by ELA and PT-neutralizing antibody by Chinese hamster ovary cell cytotoxicity neutralization (CHO). IgG anti-FHA, anti-FIM, and anti-69K antibodies were measured by EIA; unitage was calculated using the US FDA reference antiserum (#3). Pertussis agglutinins were also measured. Diphtheria antitoxin was measured by microneutralization assay and tetanus antitoxin by EIA. Antibody titers were expressed as geometric means titers; serum samples with titers less than the test detection limit were assigned a value of one-half the lower detection limit for the purpose of statistical calculations.

Statistical Analysis

Adverse reactions were analyzed after grouping for clinical significance. Rates of adverse reactions were compared by Mantel-Haenszel estimates of relative risk using center and vaccine formulation as the stratification variables. Point estimates and 95% CI of the RR were estimated in each case [31]. CI that do not include 1.00 are statistically significant.

Geometric mean antibody titers and 95% CI were computed for the antibody titer to each vaccine antigen pre- and post-immunization. Mean log titers were compared by three factor analysis of variance. The proportion of subjects achieving pre-specified levels in each group was compared by logistic regression. No adjustments were made for multiple comparisons.

A total of 545 children (44% females) were enrolled in the study, 74% of those who had completed the infant series study. The proportion of participants in this study that had received the two formulations remained 6:1 (468 APDT-high, 77 APDT-low). The mean age was 18. 9 months (range 17–21 months); all but 3 children (99.4%) completed the study.

Adverse Reactions

Rates of adverse reactions did not differ in groups immunized with APDT-high or APDT-low; rates were also similar whether immunizations were given separately at one visit, at separate visits, or in a single combined injection.

Antibody Response

Before immunization, antibody levels against all antigens except FHA were similar in children who had received APDT-high or APDT-low for their first three doses (Table 5). Children primed with APDT-high with its four-fold FHA content had significantly higher FHA titers than children immunized with APdT-low (p-0.0001). After immunization, APDT-high induced higher antibody titers than APDT-low (p=0.0001). In contrast, pre-immunization anti-PT titers measured by CHO neutralization or EIA were similar in the two groups. Paradoxically, despite twice the antigenic content, anti-PT titers were lower after immunization with APDT-high than APDT-low (p=0.038). Similarly, anti-FIM antibodies and agglutinin post-immunization were higher in the APDT-low group (p=0.01 and p=0.04, respectively) despite identical quantities of fimbrial antigen in both vaccine formulations.

Before immunization, there were few differences in antpertussis antibodies amongst the group randomized to receive the PRPT combined with APDT as a single injection or given as separate injections on the same or separate days (Table 2). Data are presented separately for recipients of APDT-high or APDT-low; however, because of the small number of children in the APDT-low group, these results will not be discussed further. The group randomized to receive separate injections on the same day had higher anti-PT antibodies by CHO neutralization than the group who were about to receive the tow injections on separate days (6.14 vs 4.80 units; p<0.05). Post-immunization antibody levels were also higher in this group (176 units) than the separate injection on separate days group (122 units; p<0.01) although similarly higher levels were found in the group given the single combined immunization (171 units; p<0.01). Anti-69K antibody response were detected in this group post-immunization, although children immunized with two injections on the same day had a higher antibody response than children immunized with the combined single vaccine and children immunized with two injections on the same day had higher antibody response than children immunized on separate days (243 vs 190 units; p<0.001) than children immunized with two injections on separate days.

Anti-PRP antibody levels were similar amongst the three groups before immunization. Post-immunization titers were higher in children immunized with separate injections on the same day (66.0 $\mu$g/ml) than in children immunized on separate days (28.4 $\mu$g/ml;p<0.001) or in children given the single combined immunization (47.1;p<0.05). The combined immunization also elicited significantly higher antibody levels than the vaccines given on separate days (p<0.05). No differences were detected amongst the groups in the percentage that achieved "protective" levels; all participants had post-immunization titers in excess of 0.15 $\mu$g/ml and only 4 participants (0–0.7%) failed to achieve a titer in excess of 1 $\mu$g/ml (3 in the group given separate injections on separate days and one in the group given the single combined injection). Over 82% of children in each group exceed a level of anti-PRP antibody of 10 $\mu$g/ml.

A vigorous antibody response was also elicited against the diphtheria and tetanus toxoids. Compared to the group given the immunization on separate days (2.1 IU/ml) significantly higher anti-diphtheria antibody levels were elicited in children immunized with two injections on the same day (3.1; p<0.01 IU/ml) or the combined single injections (3.3 IU/.ml;p<0.001). Anti-tetanus antibodies were higher in recipients of the two injections on the same day (6.7 IU/ml) than in children immunized on separate days (5.2 IU/ml;p<0.01) or children given the combined single injection (4.8 IU/ml; p<0.001). All children had post-immunization anti-diphtheria and anti-tetanus antibody titers in excess of 0.1 IU/ml, a level 10-fold the purported protective level. Over 96% of anti-tetanus titers and over 74% of anti-diphtheria titers exceeded a level of 1.0 IU/ml; there were no differences amongst the immunization groups.

Example 8

This Example describes the formulation and immunogenicity of a multi-valent combination vaccine containing inactivated polio vaccine.

Inactivated polio virus grown in MRC 5 cells was produced as follows. The cells are from kidney cells of a green monkey (*Ceropithacus aethiops*):

The trivalent poliovirus vaccine, inactivated contains Type I (Mahoney), Type II (MEF) and Type III (Saukett) components, which are grown on MRC-5 cells on microcarrier beads, processed and inactivated separately prior to combination in a trivalent vaccine.

An MRC-5 cell suspension was added to cell growth medium in a fermenter at pH 7.2 (6.9 to 7.6) and temperature 37° C.±0.5° C. Cell growth medium has the following composition:

CMRL medium 1969
Sodium bicarbonate 0.15%
Adult Bovine serum 5.00%–7.00%
Neomycin sulphate ($\mu$g of activity) 10 IU/ml
Polymyxin B 200 IU/ml CMRL medium has the following composition:

| DRY POWDER | |
|---|---|
| Ingredients | mg/liter |
| Amino Acid | |
| L-Alanine | 25.0 |
| L-Arginine (free base) | 58.0 |
| L-Aspartic Acid | 30.0 |
| L-Cysteine.HCl | 0.1 |
| L-Cystine disodium | 24.0 |
| L-Glutamic Acid.H$_2$O | 67.0 |
| L-Glutamine | 200.0 |
| L-Glycine | 50.0 |
| L-Histidine (free base) | 16.2 |
| L-Hydroxyproline | 10.0 |
| L-Isoleucine | 20.0 |
| L-Leucine | 60.0 |
| L-Lysine.HCl | 70.0 |
| L-Methionine | 15.0 |
| L-Phenylalanine | 25.0 |
| L-Proline | 40.0 |
| L-Serine | 25.0 |
| L-Threonine | 30.0 |
| L-Tryptophan | 10.0 |
| L-Tyrosine | 40.0 |
| L-Valine | 25.0 |
| Vitamins | |
| p-Aminobenzoic acid | 0.05 |
| Ascorbic acid | 0.05 |
| d-Biotin | 1.00 |
| Calcium Pantothenate | 1.00 |
| Choline dihydrogen citrate | 2.12 |
| Folic acid | 1.00 |
| Glutathione | 0.05 |
| i-Inositol | 2.00 |
| Nicotinamide | 1.00 |
| Pyridoxal.HCl | 1.00 |
| Riboflavin-5-phosphate | 0.10 |
| Thiamine HCl | 1.00 |
| Component | |
| Sodium chloride | 8000.0 |
| Potassium chloride | 400.0 |
| Calcium chloride (anhydrous) | 140.0 |
| Magnesium sulphate.7H$_2$O | 200.0 |
| Sodium phosphate, dibasic anhydrous | 180.0 |
| Sodium phosphate, nonbasic | 70.0 |
| D-glucose (anhydrous) | 1000.0 |
| Phenol red | 20.0 |

10.852 gm will yield 1 liter of Medium CMRL 1969.

The medium is prepared as follows:

450 liters of distilled pyrogen-free water are added to 905 ml of 1N hydrochloric acid. To this mixture is added 5426.5 g of CMRL 1969 dry powder with continuous stirring until dissolved to clear solution. The following chemicals are added in the order given, with continuous stirring, waiting for each chemical to dissolve before adding the next:

| Neomycin | 10 mcg/ml |
|---|---|
| Polymyxin B | 200 units/ml |
| TES Buffer Solution | 5000.0 ml |

| -continued | |
|---|---|
| Sodium Bicarbonate | 750.0 g |
| Bovine Serum | 30.0 L |

The volume was brought up to 500 L with fresh distilled water and stirred until uniformly mixed.

Cell growth is monitored and when cells are determined to be in logarithmic phase, the spent growth medium was discarded and replaced with virus growth medium. Virus growth medium has the following composition:

Chemicals of Medium 199 with Earle's salts

| Sodium bicarbonate | 0.26% |
|---|---|
| Tween 80 | 20 ppm |
| Neomycin sulphate (μg of activity) | 10 IU/ml |
| Polymyxin B | 200 IU/ml |
| L-glutamine | 100 mg/l |
| L-arginine | 29 mg/l |
| L-leucine | 30 mg/l |
| L-isoleucine | 10 mg/l |
| L-methionine | 7.5 mg/l |
| L-serine | 12.5 mg/l |
| L-threonine | 15 mg/l |
| L-cystine | 10 mg/l |
| Choline diH citrate | 107 mg/l |

CMRL 199 medium has the following composition:

| DRY POWDER | |
|---|---|
| Ingredients | mg/liter |
| L-Alanine | 25.0 |
| L-Arginine (free base) | 58.0 |
| L-Aspartic acid | 30.0 |
| L-Cysteine.HCl.H$_2$O | 0.1 |
| L-Cystine disodium | 24.0 |
| L-Glutamic acid H$_2$O | 67.0 |
| L-Glutamine | 100.0 |
| Glycine | 50.0 |
| L-Histidine (free base) | 16.2 |
| L-hydroxyproline | 10.0 |
| L-Isoleucine | 20.0 |
| L-Leucine | 60.0 |
| L-Lysine | 70.0 |
| L-Methionine | 15.0 |
| L-Phenylalanine | 25.0 |
| L-Proline | 40.0 |
| L-Serine | 25.0 |
| L-Threonine | 30.0 |
| L-Tryptophan | 10.0 |
| L-Tyrosine | 40.0 |
| L-Valine | 25.0 |
| p-Aminobenzoic acid | 0.050 |
| Ascorbic acid | 0.050 |
| d-Biotin | 0.010 |
| Calcium Pantothenate | 0.010 |
| Choline dihydrogen citrate | 1.060 |
| Folic acid | 0.010 |
| Glutathione | 0.050 |
| i-Inositol | 0.050 |
| Menadione | 0.010 |
| Nicotinamide (niacinamide) | 0.025 |
| Nicotinic acid (niacin) | 0.025 |
| Pyridoxal.HCl | 0.025 |
| Pridoxine.HCl | 0.025 |
| Riboflavin-5-phosphate | 0.010 |
| Thiamine HCl | 0.010 |
| Vitamin A acetate | 0.100 |
| Vitamin D (calciferol) | 0.100 |
| Vitamin E (-tocopherol phosphate) | 0.010 |

| -continued | |
|---|---|
| DRY POWDER | |
| Ingredients | mg/liter |
| Adenine sulphate | 10.000 |
| Adenosine triphosphate | 1.000 |
| Adenosine-5-phosphoric acid | 0.200 |
| Deoxy-2-ribose | 0.500 |
| d-Ribose | 0.500 |
| Cholesterol | 0.200 |
| Guanine | 0.300 |
| Hypoxanthine | 0.300 |

The cultures were infected with the appropriate seed virus, at a multiplicity of infection. Infection proceeds at 36° C.±1° C. When virus C.P.E. was complete, the culture was cooled to 2° C. to 15° C.

The virus harvest was clarified by filtration. The virus harvest volume was reduced by membrane ultrafiltration, with a nominal molecular weight cut off of 100,000 to a volume suitable for diafiltration against 0.04M phosphate buffer. Following diafiltration, the volume was further concentrated to a volume suitable for gel filtration. The live virus concentrate was sampled and stored at 2° C. to 8° C.

The live virus concentrate was applied to a gel filtration column and eluted from the column with 0.04M phosphate buffer. The virus fraction was collected by monitoring the optical density of the column eluate at 254 and 280 nm.

A second purification step is carried out using a DEAE-ion exchange medium, with 0.04M phosphate as the eluting buffer. This step may be repeated twice, if the amount of ion exchange medium used was insufficient, as determined by monitoring at 254 and 280 nm.

The virus fraction collected was concentrated and dialyzed against Hank's Special Medium to reduce the phosphate content. Hank's Special Medium has the following composition:

| | mg/liter |
|---|---|
| AMINO ACIDS | |
| D,L-Alanine | 25.00 |
| L-Arginine.HCl | 58.00 |
| D,L-Aspartic Acid | 30.00 |
| L-Cysteine HCl H$_2$O | 0.10 |
| L-Cystine 2HCl | 26.00 |
| D,L-Glutamic Acid | 67.00 |
| L-Glutamine | 100.00 |
| Glycine | 50.00 |
| L-Histidine HCl.H$_2$O | 16.20 |
| L-Hydroxyproline | 10.00 |
| D,L-Isoleucine | 20.00 |
| D,L-Leucine | 60.00 |
| L-Lysine.HCl | 70.00 |
| D,L-Methionine | 15.00 |
| D,L-Phenylalanine | 25.00 |
| L-Proline | 40.00 |
| D,L-Serine | 25.00 |
| D,L-Threonine | 30.00 |
| D,L-Tryptophan | 10.00 |
| L-Tyrosine (disodium salt) | 40.00 |
| D,L-Valine | 25.00 |
| VITAMINS | |
| Ascorbic Acid | 0.050 |
| d-Biotin | 0.010 |
| Vitamin D (Calciferol) | 0.100 |
| D-Calcium Pantothenate | 0.010 |

-continued

| | mg/liter |
|---|---|
| Choline Chloride | 1.060 |
| Folic Acid | 0.010 |
| i-Inositol | 0.050 |
| Mineral Salts | |
| Calcium Chloride (anhydrous) | 40.00 |
| Ferric Nitrate.9H$_2$O | 0.10 |
| Potassium Chloride | 400.00 |
| Sodium Chloride | 8000.00 |
| Magnesium Sulphate.7H$_2$O | 200.00 |
| Other Ingredients | |
| Adenine Sulphate | 10.000 |
| Adenosine triphosphate (disodium salt) | 1.000 |
| Adenylic Acid | 0.200 |
| d α Tocopherol Phosphoric Acid (sodium salt) | 0.010 |
| Cholesterol | 0.200 |
| Deoxyribose | 0.500 |
| Glucose | 1000.000 |
| Glutathione | 0.050 |
| Guanine.HCl | 0.300 |
| Hypoxanthine (sodium salt) | 0.300 |
| Ribose | 0.500 |
| Sodium Acetate.3H$_2$O | 81.500 |
| Thymine | 0.300 |
| Tween 80 | 20.000 |
| Uracil | 0.300 |
| Xanthine (sodium salt) | 0.300 |
| Menadione | 0.010 |
| Nicotinic Acid | 0.025 |
| Nicotinamide | 0.025 |
| p-Aminobenzoic Acid | 0.050 |
| Pyridoxal.HCl | 0.025 |
| Pyridoxine.HCl | 0.025 |
| Riboflavin-5-phosphate | 0.010 |
| Thiamine.HCl | 0.010 |
| Vitamin A (acetate) | 0.140 |

The purified virus fraction is filtered, through a 0.2μ porosity filter.

One or more purified virus concentrate fractions may be pooled for inactivation. Based on ELISA test results, the monovalent virus pool is diluted to:

Type I: 1750±250 DU/ml

Type II: 1500±250 DU/ml and

Type III: 1250±250 DU/ml with Hank's Special Medium.

The monovalent pool was warmed to 37° C.±1° C., then filtered through a 0.2μ porosity filter.

The required amount of formalin, to achieve a 1:4000 concentration, was added. The virus pool and formalin are mixed and stirred continuously at 37° C.±1° C. The monovalent virus pool is sampled for viability. On the sixth day, the inactivating virus pool is filtered through a 0.2μ filter and maintained at 37° C.±1° C. On the thirteenth day of inactivation, the virus pool is filtered through a 0.2μ filter.

One or more inactivated monovalent components are selected and aseptically connected to a pooling tank. The monovalent pool was further concentrated, by membrane ultrafiltration, with a nominal molecular weight cut off of 100,000. Dialysis, against RIV-PBS diluent:

Disodium Hydrogen Phosphate (Na$_2$HPO$_4$), 0.346 g/CCmL

Potassium Dihydrogen Phosphate (KH$_2$PO$_4$), 0.187 g/CCmL with Tween was then carried out to achieve uniformity of the final product.

Albumin (human) was added to achieve a final concentration of 0.5%. The pooled monovalent concentrate was then filtered through a 0.2μ filter. RIV-PBS diluent with Tween is added to achieve an estimated (by calculation), concentration of 10 to 15 doses per 0.5 ml. The pooled concentrate is stored at 2° C. to 8° C. until required.

The appropriate volumes of Types I, II and III monovalent components were calculated and combined. The trivalent vaccine is targeted to contain:

Type I: 40 DU/0.5 ml dose

Type II: 8 DU/0.5 ml dose

Type III: 32 DU/0.5 ml dose

Trivalent concentrate is stored at 2° C. to 8° C. until used. Formaldehyde and 2-phenoxyethanol are added and mixed. Albumin (human) is added, by calculation, to give a final concentration of 0.5%.

Alternatively, inactivated poliovirus grown on Vero cells was produced as follows:

Ampoules of the Vero working cell bank are subcultivated up to the level of chosen cellular passage. The cell ampoules are preserved in liquid nitrogen. Cells are grown using micro-support beads which are spherical beads of an average diameter of about 100 micrometers, constituted by Dextran polymers having radicles of DEAE grafted on their surface (diethylaminoethyl), giving them a positive charge.

The basic medium for cellular growth is the "Minimum Essential Medium" (MEM) of Eagle in Earle saline solution enriched with 0.2% of lactalbumin hydrolysate, 0.1% of dextrose, 5% of calf serum. Each ml of medium contains the following antibiotics:

| Steptomycin: | 75 units per ml |
|---|---|
| Neomycin: | 14 units per ml |
| Polymyxin B sulphate: | 35 units per ml |

The Vero cells are progressively subcultivated in Biogenerators of increasing size. Then, the culture medium and the sufficient volume of microsupport beads per liter of medium are introduced in the industrial biogenerator. The temperature is stabilized at +37° C. The cells collected by trypsination are added and put under stirring. The culture is continued during 4 to 7 days at +37° C., the stirring being progressively increased. Usually, at the end of the culture, an increase of 6 to 20 times in the cellular growth is observed. The medium used for the virus growth is medium 199 (Parker) in Earle saline solution, enriched with 0.1% of dextrose. It contains the same antibiotics, at the same concentration as the medium of cellular growth, but it does not contain calf serum. On the 4th/7th day of cellular growth, the biogenerator stirring at the industrial stage, is stopped; the beads settle at the bottom of the tank, the old medium is removed. Some medium 199 free of serum is then introduced in each biogenerator and stirred. This medium is then drawn off. This stage corresponds to a washing of the beads+cells. Some medium 199 free of serum is transferred into the biogenerator together with the necessary volume of seed lot. The virus is adsorbed into the cells by gentle stirring. At the end of the virus culture, the stirring is stopped. The virus suspension is drawn off and collected and the beads are retained by filtration. The virus suspension is homogenized. The harvest, filtered on an organic membrane of medium size pores at 0.20 mm is stored at +4° C. The virus is concentrated by ultrafiltration.

The virus is further purified by ion exchange chromatography using DEAE-dextran-Spherosil support, balanced with phosphate buffer 0.04 M, pH=7.00. The virus is further purified by gel filtration using chromatography. A column of molecular sifting (gel filtration) containing an agarose gel, Sepharosis CL-6B for instance, balanced with phosphate 0.04 M, pH=7.00. The virus is further purified by chromatography using DEAE dextran-Spherosil, balanced with a phosphate buffer 0.04 M, pH=7.00. As soon as the last purification is performed, the virus suspension is adjusted to the required volume with some medium M-199, pH=7.0 without phosphate, concentrated ten times in EDTA 5 mm, glycine at 0.5% and Tween 80 at a final concentration of 50 mg/liter (Inactivation Medium). This mixture constitutes the "Concentrated Virus Mixture". It is filtered on a membrane of 0.2 µm. The concentrated virus suspension is stored at +4° C. pending inactivation.

One or several lots of "Concentrated Virus Mixture" of the same type are mixed and possibly diluted or adjusted with some "Inactivation Medium" in a suitable tank. The dilution is adjusted to the right volume according to the types in order to obtain a D antigen titre between:

1500 and 2000 D units in type 1
800 and 1000 D units in type 2
1000 and 1500 D units in type 3 and a protein rate according to the requirement iii, that is to say:

| |
|---|
| ≤40 µg/ml in type 1 |
| ≤70 µg/ml in type 2 |
| ≤30 µg/ml in type 3. |

The adjusted purified concentrated virus suspension is filtered on a 0.22 µm membrane at most 72 hours before the beginning of inactivation. The virus suspension is then warmed up again at +37° C. For inactivation, formaldehyde solution is added to obtain a concentration at 1/4000. In order to follow the inactivation kinetics after 24, 48, 72 and 96 hours, samples are taken off during the first four days. A 10 ml sampling is performed with immediate neutralization of the formaldehyde by action of sodium bisulphite and direct storage at −20° C. pending titration.

On the 6th day, the virus suspension during inactivation was filtered using a 0.22 µm filter. After filtration, the incubation of the liquid is carried on at +37° C. for 6 more days with a constant stirring. On the 9th day of inactivation, 3 times the volume corresponding to 3000 human doses and 500 mL minimum of the crude individual harvest is taken off. This volume is calculated according to the titre in D antigen of the "Concentrated Virus Mixture. The sampling is directly neutralized with some sodium bisulphite to stop the action of the residual formaldehyde. The homogenized and inactivated virus suspension is then taken out from the incubator at +37° C. after 12th day's inactivation. The volume is directly neutralized with some sodium bisulphite and stored at +4° C.

To prepare a concentrated trivalent lot of IPV monovalent preparations were combined to provide:

| | |
|---|---|
| Type 1 (Mahoney) | 400 antigen D units |
| Type 2 (MEF-1) | 80 antigen D units |
| Type 3 (Saukett) | 320 antigen D units |

Medium 199—pH 7.2 q.s. to 1 ml
The mixture was stirred to homogenize filtered on a membrane of porosity 0.22 microm.

The final bulk product is obtained from the concentrated trivalent bulk lots such as those described, by dilution with medium 199, pH 7.2, without phenol red so that the unit dose contains per 0.5 ml.

40 units of D antigen for type 1
8 units of D antigen for type 2
32 units of D antigen for type 3.

An APDT contained five pertussis antigens (10 µg PT, 5 µg FHA, 5 µg FIM 2 and 3, 3 µg 69K), 15 Lf diphtheria toxoid, 5 Lf tetanus toxoid, 1.5 mg aluminum phosphate as adjuvant and 0.6% 2-phenoxyethanol as preservative per 0.5 ml (CLASSIC). The vaccine was used alone or in combination with either IPV produced on MRC-5 cells (mIPV; Connaught Laboratories Limited), IPV produced on Vero cells (vIPV; Pasteur-Merieux Serums et Vaccins, Lyon, France), or with OPV (Connaught Laboratories Limited). In order not to disrupt their routine immunization schedule, *Haemophilus influenzae* b-tetanus toxoid conjugate vaccine was administered at the time of the follow up visit.

Population

Healthy 17 to 19 month old children who had been immunized with three doses of DTP and 2 doses of OPV, or 3 doses of DTP-IPV prior to 5 months of age were recruited into the study. Following written informed consent from parents or guardians, children were allocated by a computer-generated balanced block list of random numbers to receive one of five vaccine regimens (Table 1). Combination vaccines containing A3DT were given by the intramuscular route with a 25 mm needle into the deltoid muscle of the arm or the vastus lateralis muscle of the thigh if the deltoid was of insufficient mass. IPV (0.5 ml; mIPV or vIPV) when given alone were administered by the subcutaneous route using a needle ½ to ⅝ inch (12.5–16 mm) in length, APDT containing vaccines were given into the left limb; the right limb was used for the inactivated poliovirus vaccines when given separately and for all *Haemophilus influenzae* b-conjugate vaccines at the second visit.

Clinical and Laboratory Monitoring

Blood samples were collected by venipuncture or by finger-prick prior to and 28 days after the immunization. IgG antibodies to PT were measured by enzyme immunoassay and PT-neutralizing antibody by CHO neutralization. IgG anti-FHA, anti-FIM, and anti-69K antibodies were measured by enzyme immunoassay; units were calculated using the US FDA reference antiserum (#3). Pertussis agglutinins were also measured. Diphtheria antitoxin was measured by microneutralization assay and tetanus antitoxin by immunoassay. Antibody-poliovirus type 1, 2 and 3 antibodies were measured by viral neutralization. Antibody titers were expressed as geometric mean titers; serum samples with titers less than the test detection limit were assigned a value of one-half the lower detection limit for tile purpose of statistical calculations.

Geometric mean antibody titers and 95% confidence intervals were computed for the antibody titer to each vaccine antigen pre- and post-immunization. Mean log titers and mean log-fold antibody titer rises were compared by profile analysis and analysis of variance. The proportion of subjects achieving pre-specified levels in each group was compared by logistic regression. Comparisons were made between each poliovirus vaccine given separately or as a combined injection, between mIPV and vIPV (both separately and combined) and between the combined IPV vaccines and OPV. No adjustments were made for multiple comparisons.

A total of 425 children (52% female) were enrolled in the study and received the booster immunization (Table 6). The mean age at enrollment was 17.8 months (range 17.0–20.0). Post-immunization serum specimens were obtained from 422 (99.3%) participants a mean of 29.2 days after immunization (range 28–41 days). Adverse events categorized as severe were uncommon in the study.

Before immunization, antibody levels were equivalent amongst the groups for most antigens (Table 7). Exceptions were that participants allocated to receive APDT and mIPV as separate injections had significantly lower anti-FIM, agglutinin, anti-diphtheria and anti-tetanus antibody levels than the group allocated to receive the combined APDT-mIPV vaccine. Similarly, the group randomized to receive the separate injections of APDT and vIPV had lower anti-tetanus antibody levels than the group about to receive the combined APDT-vIPV.

After immunization, there was a significant antibody rise in all vaccine groups against all antigens included in the vaccines (Table 7). There were few differences in the antibody response to pertussis antigens depending on the polio vaccine group. There were no differences in anti-PT antibody by enzyme immunoassay or CHO neutralization or in anti-FHA antibodies. Anti-69K antibodies were significantly higher in the group given the mIPV vaccine combined with APDT (77.7 units) than the group given mIPV as a separate injection (37.9 units; $p<0.001$) or the group given OPV (47.7; $p<0.05$). Anti-FIM antibodies and agglutinins were also higher in the group given the combined APDT-mIPV group than the group given separate injections; however, these same differences were also detected in the pre-immunization sera.

Differences were detected in the anti-poliovirus antibody responses. Both APDT-mIPV and APDT-vIPV elicited higher anti-poliovirus type 1 and type 3 antibodies ($P<0.001$ for all comparisons). Anti-poliovirus type 2 antibody levels were also higher after APDT-mIPV (10,633 reciprocal dilution) and APDT-vIPV (10,256) than OPV (7185); however, this only reached statistical significance for APDT-mIPV ($p<0.05$). The anti-poliovirus antibody titers achieved with combined APDT-MIPV were also higher than when the mIPV was given as a separate injection (6620-1 $p<0.05$).

Anti-tetanus antibody titers were higher in recipients of OPV than either of the IPV combinations ($p<0.05$). Anti-diphtheria titers were also higher in OPV recipients but this only reached statistical significance compared to the APDT-vIPV group ($p<0.05$). After immunization, all children had antibody levels against diphtheria and tetanus in excess of 0.01 IU/ml and all but one child had levels in excess of 0.1 IU/mi.

The results of this study demonstrate that an acellular Pertussis vaccine containing PT, FHA, 69K, and FIM combined with diphtheria and tetanus toxoids can also be combined with inactivated poliovirus vaccine without any significant increase in reactogenicity or loss of immunogenicity. In contrast to the results with the whole cell DTP, there was not diminution of the antibody response to *Bordetella pertussis* antigens. There were no substantive differences between the IPV vaccines prepared on either MRC-5 or Vero cell lines; both vaccines induced higher serum anti-poliovirus antibody levels than OPV. The demonstration of the equivalence of mIPV and vIPV facilitates the implementation of the acellular pertussis vaccine in jurisdictions with a preference for an IPV derived from a particular cell line.

In conclusion, this demonstrates that a five component acellular pertussis vaccine can be safely combined with either of two IPV vaccines for the fourth vaccine dose between 17 and 19 months of age. Additional studies are required to assess the combinations in infants and in combination with the *Haemophilus influenzae* b-conjugate vaccines.

SUMMARY OF DISCLOSURE

In summary of this disclosure, the present invention provides novel preparations of Bordetella and non-Bordetella antigens to produce a multi-component pertussis vaccines. Such vaccines are safe, non-reactogenic, immunogenic and protective in humans. Modifications are possible within the scope of this invention.

TABLE 1

Acellular Pertussis Vaccines

| Vaccine | PT | Toxoiding Agent | FHA | P.69 | AGG2 | AGG3 | Reference |
|---|---|---|---|---|---|---|---|
| AMVC | + | $H_2O_2$[a] | − | − | − | − | 62 |
| Mass PHL[b] | + | TMN[c] | − | − | − | − | 63 |
| Institut Mérieux | + | GI[d] | + | − | − | − | 64 |
| Smith-Kline | + | FI[e]/GI | + | − | − | − | 32 |
|  | + | FI/GI | + | + | − | − | 32 |
| CAMR[f] | + | FI | + | − | + | + | 65 |
| Lederle/ Takeda | + | FI | + | + | + | − | 66 |
| Connaught | + | GI | + | − | + | + | 32 |
|  | + | GI | + | + | + | + | 67 |

[a]Hydrogen peroxide inactivated.
[b]Massachusetts Public Health Laboratories.
[c]TNM, tetranitromethane-inactivated.
[d]GI, glutaraldehyde-inactivated.
[e]FI, formalin-inactivated.
[f]Centre for Applied Microbiology and Research.

TABLE 2

IgG antibody responses to pertussis antigen and diphtheria and tetanus toxoids in adults and young children after immunization with placebo or acellular pertussis (AP), diphtheria-tetanus-pertussis (DTP), or multicomponent acellular DTP (ADTP) toxoids.

| | Adults | | | |
|---|---|---|---|---|
| | Before Immunization | | Postimmunization day 28 | |
| | Placebo | AP $CP_{18/5/5/3}$ | Placebo | AP $CP_{18/5/5/3}$ |
| Pertussis toxoid | 16.45 (9.46–28.62) | 22.78 (12.11–42.86) | 16.56 (9.08–30.22) | 415.87 (243.91–709.09) |
| Filamentous hemagglutinin | 15.24 (10.28–22.60) | 23.59 (15.59–35.69) | 13.36 (7.71–23.16) | 317.37 (243.85–141.41) |

TABLE 2-continued

IgG antibody responses to pertussis antigen and diphtheria and tetanus toxoids in adults and young children after immunization with placebo or acellular pertussis (AP), diphtheria-tetanus-pertussis (DTP), or multicomponent acellular DTP (ADTP) toxoids.

| | | | | |
|---|---|---|---|---|
| Agglutinogens | 21.26 | 28.64 | 27.0 | 2048.00 |
| | (12.14–32.23) | (12.20–67.21) | (15.37–47.78) | (1025.62–4089.55) |
| Pertactin | 7.89 | 11.47 | 7.46 | 855.13 |
| | (4.00–15.56) | (6.41–20.55) | (3.51–16.87) | (396.41–1844.67) |
| CHO cell | 12.30 | 21.11 | 10.78 | 604.67 |
| neutralizing | (6.97–21.68) | (10.35–43.06) | (5.54–20.97) | (403.82–405.41) |
| assay | | | | |
| Diphtheria toxoid | <0.1 | <0.1 | <0.1 | <0.1 |
| Tetanus toxoid | <0.1 | <0.1 | <0.1 | <0.1 |
| No. studied | 16 | 15 | 16 | 15 |

| | Children | | | |
|---|---|---|---|---|
| | Before Immunization | | After Immunization | |
| | DTP | ADTP $CP_{18/10/5/3}DT$ | DTP | ADTP $CP_{10/18/8/3}DT$ |
| Pertussis toxoid | 43.71 | 15.45 | 221.32 | 306.55 |
| | (14.29–133.88) | (8.50–28.10) | (99.83–490.67) | (155.84–603.03) |
| Filamentous | 2.93 | 3.86 | 30.06 | 29.86 |
| hemagglutinin | (1.81–4.73) | (3.03–4.93) | (11.02–76.46) | (16.51–53.99) |
| Agglutinogens | 26.72 | 29.24 | 315.2 | 1243.3 |
| | (16.94–42.15) | (13.63–62.75) | (127.4–779.9) | (594.8–2603.5) |
| Pertactin | 6.54 | 9.45 | 60.13 | 118.16 |
| | (2.79–15.33) | (5.50–16.23) | (24.59–147.04) | (57.87–233.19) |
| CHO cell | 27.47 | 9.71 | 218.66 | 342.51 |
| neutralizing | (7.36–102.62) | (4.71–20.03) | (24.6–1100.8) | (146.6–600.2) |
| assay | | | | |
| Diphtheria toxoid | <0.1 | <0.1 | 8.75 | 9.65 |
| | | | (6.52–23.92) | (5.62–16.57) |
| Tetanus toxoid | <0.1 | <0.1 | 4.31 | 6.32 |
| | | | (3.20–5.28) | (5.31–7.53) |
| No. studied | 10 | 25 | 12 | 25 |

Data are expressed as geometric mean with 95% confidence intervals. For pertussis toxoid, filamentous hemagglutinin, agglutinogens, pertactin, and diphtheria and tetanus toxoids, antibody titers expressed as ELISA units/nL. For CHO cell neutralizing assay, values reflect reciprocal of highest dilution demonstrating 80% neutralization.

TABLE 3

Serulogic Results of Acellular Pertussis Vaccines In Infants (2, 4 and 6 Months Old)

| | | | | Geometric Mean Titres | | | | | | | |
|---|---|---|---|---|---|---|---|---|---|---|---|
| Clinical Trial | Product | Study | Number of Participants | PT | FHA | 69 kDa | Fimbrial agglutinogens | CHO Cell Neutralization | Agglutination | Tet | Dip |
| 1 | $CP_{10/3/5}DT$ | U.S. NIAID | 108 | 38 | 37 | 3 | 229 | 160 | 85 | 7.8 | 0.8 |
| | $CP_{10/3/5/4}DT$ | Multicentre | 113 | 36 | 36 | 113 | 241 | 150 | 73 | 5.0 | 0.4 |
| | Whole Cell (Mass.) | Comparative Study | 95 | 20 | 51 | 101 | 70 | 80 | 42 | — | — |
| | Whole Cell (Lederle) | (Cycle I) | 312 | 67 | 3 | 64 | 193 | 270 | 84 | — | — |
| 2 | $CP_{10/5/3/4}DT$ | Phase II | 315 | 87.1 | 50.2 | 29.9 | 239.8 | 29.6 | — | 1.5 | 0.3 |
| | Whole Cell (CLL) | Canada | 101 | 20 | 4.7 | 6.4 | 603.2 | 2.6 | — | 1.2 | 0.4 |
| 3 | $CP_{10/5/5/3}DT$ | Phase IIB | 32 | 58.4 | 45.2 | 40.6 | 111.4 | 32.7 | — | 1.0 | 0.14 |
| | $CP_{20/20/5/3}DT$ | Canada | 33 | 133.3 | 95.0 | 37.1 | 203.8 | 82.4 | — | 1.1 | 0.21 |
| | Whole Cell (CLL) | | 30 | 10.4 | 8.9 | 6.8 | 393.9 | 4.0 | | 1.8 | 0.31 |
| 4 | $CP_{10/5/5/3}DT$ | Phase IIC | 42 | 105.1 | 82.5 | 71.1 | 358.6 | 66.9 | 307.0 | 2.0 | 0.33 |
| | $CP_{20/20/5/3}DT$ | Canada | 250 | 101.6 | 163.9 | 87.6 | 220.6 | 68.7 | 219.2 | 1.8 | 0.38 |
| 5 | $CP_{20/20/5/3}DT$ | Montreal | 58 | 212.7 | 83.4 | 106.3 | 601.9 | 109.6 | — | 1.9 | 0.53 |
| | Whole Cell (CLL) | Feasibility Study | 58 | 101.4 | 11.7 | 16.8 | 906.9 | 6.0 | | 1.1 | 0.27 |
| 6 | $CP_{10/5/3}DT$ | U.S. NIAID | 80 | 42 | 34 | 50 | 310 | 196 | 185 | | |
| | $CP_{20/20/5/3}DT$ | Comparative Study | 80 | 39 | 87 | 43 | 184 | 254 | 137 | — | — |
| | Whole Cell (CLI) | (Cycle II) | 80 | 2 | 3 | 9 | 33 | 54 | 167 | | |
| | Whole Cell (Lederle) | | 80 | 18 | 2 | 16 | 129 | 137 | 86 | | |

CLI — Connaught Laboratories Incorporated, Swiftwater, Pennsylvania.
CLL — Connaught Laboratories Limited, Willowdale, Ontario.
Mass — Massachusetts Public Laboratories.
Lederle — Lederle Laboratories Inc.

TABLE 4

Efficacy of Acellular Pertussis Vaccines

| Vaccine | Efficacy % A | B |
|---|---|---|
| $CP_{10/5/6/3}DT$ | 84.7 (80.3→88.5)[1] | 77 |
| $PT_{25}.FHA_{25}DT$ | 58 (49.8→64.8)[2] | |
| $DPT^2$ | 47.9 (37.1→56.9)[3] | |

A: case definition: 21 day spasmodic cough and culture positive
B: case definition: mild pertussis cough of at least one day
Note 1: confidence limits
Note 2: whole cell pertussis vaccine

TABLE 5

| VACCINE | N | GMT (95% CI) | % ≥ 0.15 | % ≥ 1.0 |
|---|---|---|---|---|
| HCPDT-vIPV-PRP-T (liquid) | 327 | 4.76 (4.12–5.50) | 97.9 | 88.4 |
| HCPDT-mIPV to reconstitute PRP-T | 322 | 4.37 (3.74–5.09) | 98.4 | 84.5 |
| HCPDT-mIPV and PRP-T (separate) | 108 | 3.83 (3.05–4.80) | 100 | 88.9 |
| DPT-IPV to reconstitute PRP-T | 105 | 3.84 (2.96–5.07) | 97.1 | 81.0 |

TABLE 6

| VACCINE | N | POLIO 1 | POLIO 2 | POLIO 3 |
|---|---|---|---|---|
| HCPDT-vIPV-PRP-T (liquid) | 328 | 624 (533–732) | 2,397 (2,043–2,814) | 1,268 (1,082–1,485) |
| HCPDT-mIPV to reconstitute PRP-T | 323 | 718 (589–875) | 2,173 (1,837–2,570) | 1,938 (1,640–2,291) |
| HCPDT-mIPV and PRP-T (separate) | 108 | 702 (513–960) | 2,595 (2,005–3,360) | 1,837 (1,362–2,477) |
| DPT-mIPV to reconstitute PRP-T | 105 | 889 (630–1,255) | 2,597 (2,000–3,373) | 2,726 (2,108–3,525) |

TABLE 7

| ANTIGEN | HCPDT-vIPV-PRP-T (liquid) (n = 324) | HCPDT-mIPV to reconstitute PRP-T (n = 322) | HCPDT-mIPV and PRP-T (separate) (n = 108) | DPT-mIPV to reconstitute PRP-T (n = 105) |
|---|---|---|---|---|
| PT | 86.7 (80.9–93.0) | 89.1 (82.5–96.1) | 102.6 (90.5–116.4) | 15.2 (12.2–19.0) |
| FHA | 155.7 (147.2–164.7) | 152.5 (143.6–162.0) | 165.3 (148.4–184.3) | 31.4 (27.2–36.2) |
| FIM | 276.2 (242.2–315.1) | 244.5 (211.4–282.7) | 355.0 (279.4–451.1) | 323.3 (264.6–417.3) |
| Pertactin | 55.2 (48.7–62.5) | 56.0 (49.4–63.4) | 40.5 (33.0–49.7) | 8.9 (6.8–11.7) |
| DIPH | 0.29 (0.25–0.33) | 0.28 (0.24–0.33) | 0.36 (0.28–0.46) | 0.29 (0.22–0.38) |
| TET | 1.09 (1.00–1.19) | 0.88 (0.80–0.96) | 1.61 (1.40–1.86) | 0.63 (0.51–0.78) |

TABLE 8

| ANTIGEN | HCPDT-vIPV 1 injection (n = 85) | HCPDT + vIPV 2 injections (n = 84) | HCPDT-mIPV 1 injection (n = 87) | HCPDT + mIPV 2 injections (n = 81) | HCPDT + OPV HYBRID + OPV (n = 85) |
|---|---|---|---|---|---|
| Diphtheria | 4.1[e] | 4.57 | 4.99 | 3.89 | 6.19[e] |
| Tetanus | $.17[g] | 3.13 | 3.25[f] | 3.31 | 4.02[fg] |
| PT | 73.9 | 68.2 | 80.5 | 65.2 | 86.8 |
| FHA | 93.9 | 98.1 | 112.8 | 117.8 | 120.9 |
| Pertactin | 63.8 | 45.1 | 77.7[ab] | 37.9[a] | 47.7[b] |
| FIM | 922.7 | 809.1 | 1210[c] | 753.3[c] | 1215 |
| Agglutinins | 1278 | 1285 | 1606[d] | 1040[d] | 1532 |
| Polio type 1 | 6672[i] | 5681 | 10242[h] | 8784 | 2110[hi] |
| Polio type 2 | 10256 | 7861 | 10633[jk] | 6620[j] | 7185[k] |
| Polio type 3 | 5771[m] | 7781 | 6798[l] | 8541 | 556.3[lm] |

TABLE 9

Combining PRP-T with Component Pertusis Vaccine when given Combined or Separate on the Same or Separate Days $CP_{105/30}DT$ (CLASSIC) and $CP_{20/20/5/3}DT$ (HYBRID) at 19 months (1 month post)

| ANTIGEN | Classic/Hybrid to reconstitute PRP-T single injection (n = 181) | Classic/Hybrid & PRP-T separate injection same day (n = 181) | Classic/Hybrid & PRP-T separate injections separate days (n = 180) |
|---|---|---|---|
| anti-PRP | 59.3[a] | 60.8[b] | 32.4[ab] |
| Diphtheria | 3.7[c] | 3.3[bd] | 2.4[cd] |
| Tetanus | 5.0[e] | 6.6[ef] | 5.3[f] |
| PT | 120[g] | 114[h] | 96.1[gh] |
| CHO | 195[i] | 189[f] | 136[if] |
| FHA | 102 | 99.3 | 87.5 |
| Pertactin | 187 | 223[d] | 168[k] |
| FIM | 430[f] | 434[m] | 315[lm] |
| Agglutinins | 1004 | 1033 | 682 |

Note: values with matching letters differed significantly (p ≤ 0.05)

REFERENCES

1. Muller, A. S. Leeuwenburg, J. and Pratt, D. S. (1986) Pertussis: epidemiology and control. *Bull WHO* 64: 321–331.
2. Fine, P. E. M. and Clarkson, J. A. (1984). Distribution and immunity to pertussis in the population of England and Wales. *J. Hyg.* 92:21–26.
3. Mortimer, E. A. Jr. (1990). Pertussis and its prevention: a family affair. *J. Infect. Dis.* 161: 473–479.
4. Addiss, D. G., Davis, I. P., Meade, B. D., Burstyn, D. G. Meissner, M., Zastrow, J. A., Berg, J. L., Drinka, P., and Phillips, R. (1991). A pertussis outbreak in a Wisconsin nursing home. *J. Infect. Dis.* 164: 704–710.
5. Halperin, S. A. and Marrie, T. J. (1991a). Pertussis encephalopathy in an adult: case report and review. *Rev. Infect. Dis.* 13: 1043–1047.
6. Onorato, I. M., Wassilak, S. G. and Meade, B. (1992). Efficacy of whole-cell pertussis vaccine in preschool children in the United States. *JAMA* 267: 2745–2749.
7. Miller, D. L., Ross, E. M., Alderslade, R., Bellman, M. H., and Brawson, N. S. B. (1981). Pertussis immunization and serious acute neurological illness in children. *Brit Med. J.* 282: 1595–1599.
8. Tamura, M., Nogimort, K., Murai, S., Yajima, M., Ito, K., Katada, T., Ui, M., and Ishii, S. (1982). Subunit structure of islet-activating protein. pertussis toxin, in conformity with the A-B model. *Biochemistry* 21: 5516–5522.
9. Tuomanen, E. and Weiss, A. (1985). Characterization of two adhesins of *Bordetella pertussis* for human ciliated respiratory epithelial cells. *J. Infect. Dis.* 152:118–125.
10. Friedman, R-L., Nordeneson, K., Wilson, L., Akporiaye, E. T., and Yocum D. E. (1992). Uptake and intracellular survival of *Bordetella pertussis* in human macrophages. *Infect. Immun.* 60: 4578–4585
11. Pittman, M (1979). Pertussis toxin: the cause of the harmful effects and prolonged immunity of whooping cough. A hypothesis. *Rev. Infect. Dis.*, 1: 401–402
12. Granstrom, M. and Granstrom G. (1993). Serological correlates in whooping cough. *Vaccine* 11:445–448.
13. Gearing, A. J. H., Bird, C. R., Redhead, K., and Thomas, M. (1989). Human cellular immune responses to *Bordetella pertussis* infection. *FEMS Microbial. Immunol.* 47: 205–212.
14. Thomas, M. G., Redhead, K., and Lambert, H. P. (1989a). Human serum antibody responses to *Bordetella pertussis* infection and pertussis vaccination. *J. Infect. Dis.* 159: 211–218.
15. Thomas, M. G., Ashworth, L. A. E., Miller, E., and Lambert, H. P. (1989b). Serum IgG, IgA, and IgM responses to pertussis toxin, filamentous haemagglutinin, and agglutinogens 2 and 3 after infection with *Bordetella pertussis* and immunization with whole-cell pertussis vaccine. *J. Infect. Dis.* 160: 838–845.
16. Tomoda, T., Ogura, H., and Kurashige, T. (1991). Immune responses to *Bordetella pertussis* infection and vaccination. *J. Infect. Dis.* 163: 559–563.
17. Petersen, J. W., Ibsen. P. H., Haslov, K., Capiau, C., and Heron, I. (1992a). Proliferative responses and gamma interferon and tumor necrosis factor production by lymphocytes isolated from trachcobroncheal lymph nodes and spleens of mice aerosol infected with *Bordetella pertussis*. *Infect. Immun.* 60: 4563–4570
18. Englund, J. A., Reed, G. F., Edwards, K. M., Decker, D., Pichichero, M. E., Ronnels, M. B., Steinhoff, M. C., Anderson, E. L., Meade, B. D., Deloria, M. A., and the NIAID Acellular Pertussis Vaccine Group. (1992b). Effect of transplacental antibody and development of pertussis toxin (PI) and filamentous haemagglutinin (FHA) antibody after acellular (AC) and whole cell (WC) pertussis vaccines in infants. *Pediat. Res.* 31:91A.
19. Oda, M., Cowell, J. L., Burstyn, D. G., Thaib, S., and Manclark, C. R. (1985). Antibodies to *Bordetella pertussis* in human colostrum and their protective activity against aerosol infection of mice. *Infect. Immun.* 47:441–445.
20. Petersen, J. W., P. H. Bentzon, M. W., Capiau, C., and Heron, I. (1991). The cell mediated and humoral immune response to vaccination with acellular and whole cell pertussis vaccine in adult humans. *FEMS Microbiol Lett.* 76: 279–288.
21. Oda, M., Cowell. J. L., Burstyn, D. G., and Manclark, C. R. (1984). Protective activities of the filamentous haemagglutinin and the lymphocytosis-promoting factor of *Bordetella pertussis* in mice. *J. Infect. Dis.* 150: 823–833.
22. Sato, H., Ito, A., Chiba, J. and Sato, Y. (1984b). Monoclonal antibody against pertussis toxin: effect on toxin activity and pertussis infections. *Infect. Immun.* 46: 422–428.
23. Sato, H. and Sato, Y. (1990). Protective activities in mice of monoclonal antibodies against pertussis toxin. *Infect. Immun.* 58: 3369–3374.
24. Weiss, A. A. and Hewlett, E. L. (1986). Virulence factors of *Bordetella pertussis*. *Ann. Rev. Microbiol* 40: 661–668.
25. Munoz, J. J. (1988). Action of pertussigen (pertussis toxin) on the host immune system. In: *Pathogenesis and Immunity in Pertussis*. A. C. Wardlaw and R. Parton, eds., John Wiley & Sons Ltd., Toronto. pp. 211–229.
26. Watkins, P. A., Burns, D. L., Kanaho, Y., Liu, T-Y., Hewlett E. L., and Moss, J. (1985). ADP-ribosylation of transducin by pertussis toxin. *J. Biol. Chem.* 260: 13478–13482.
27. Burns, D. L., Kenimer, J. G., and Manclark, C. R. (1987). Role of the A subunit of periussis toxin in alteration of Chinese hamster ovary cell morphology. *Infect. Immun.*, 55: 24–28.
28. Munoz, J. J., Arai, H., and Cole, R. L. (1981). Mouse-protecting and histamine-sensitizing activities of pertus-sigen and fimbrial hemagglutinins from *Bordetella pertussis*. *Infect. Immun.* 32: 243–250.
29. Relman, D. A., Domenighini, M., Tuomanen, E., Rappuoli, R., and Falkow, S. (1989). Filamentous haemagglutonin of *Bordetella pertussis*: nucleotide sequence and crucial role inadherence. *Proc. Natl. Acad. Sci. USA* 86: 2637–2641.
30. Di Tommaso, A., Domenighini, M., Bugnoli, M., Tagliabuc, A., Rappuoli, R., and De Magistris, M. T. (1991). Identification of subregions of *Bordetella pertussis* filamentous haemagglutonin that stimulate human T-cell responses. *Infect. Immun.* 59: 3313–3315.
31. Tomoda, T., Ogura, H., and Kurashige, T. (1992). The longevity of the immune response to filamentous haemagglutonin and pertussis toxin in patients with pertussis in a semiclosed community. *J. Infect. Dis.* 166: 908–910.
32. Edwards, K. M., Meade, B. D., Decker, M. D., Reed, G. F., Rennels, M. B., Steinhoff, M. C., Anderson, E. L., Englund, J. A., Pichichero, M. E., Deloria, M. A., Deforest, A., and the NIAID Acellular Pertussis Vaccine Study Group (1992). Comparison of thirteen acellular pertussis vaccines: serological response. *Pediatr. Res.* 31:91A.
33. Kimura, A., Mountzoutos, K. T., Relman, D. A., Falkow, S., and Cowell, J. L. (1990a). *Bordetella pertussis* filamentous haemagglutonin: evaluation as a protective antigen and colonization factor in a mouse respiratory infection model. *Infect. Immun.* 58:7–16.
34. Shahin, R. D., Amsbaugh, D. F., and Leef, M. F. (1992). Mucosal immunization with filamentous haemagglutonin protects against *Bordetella pertussis* respiratory infection. *Infect. Immun.* 60: 1482–1488.
35. Montaraz, J. A., Novotny, P., and Ivanyi, J. (1985). Identification of a 68-kilodalton protective protein antigen from *Bordetella bronchiseptica*. *Infect. Immun.* 161: 581–582.
36. Leininger, E., Roberts, M., Kenimer, J. G., Charles, I. G., Fairweather, M., Novotny, P., and Brennan, M. J (1991). Pertactin, and Arg-Gly-Asp-containing *Bordetella pertussis* surface protein that promotes adherence of mammalian cells. *Proc. Natl. Acad Sci. USA* 88: 345–349.
37. De Magistris, T., Romano, M., Nuti, S., Rappuoli, R. and Tagliabue, A. (1988). Dissecting human T responses against Bordetella species *J. Exp. Med.* 168: 1351–1362.
38. Seddon, P. C., Novotny, P., Hall, C. A., and Smith, C. S. (1990). Systemic and mucosal antibody response to *Bordetella pertussis* antigens in children with whooping cough. *Serodiagnosis Immunother. Inf. Dis.* 3: 337–343.
39. Podda, A., Nencioni, L., Marsili, I., Peppoloni, S., Volpini, G., Donati, D., Di Tommaso, A., De Magistris, M. T., and Rappuoli, R. (1991). Phase I clinical trial of an 39. acellular pertussis vaccine composed of genetically detoxified pertussis toxin combined with FHA and 69 kDa. *Vaccine* 9: 741–745.
40. Roberts, M., Tite, J. P., Fairweather, N. F., Dougan G. and Charles, I. G. (1992). Recombinant P.69/pertactin: immunogenicity and protection of mice against *Bordetella pertussis* infection. *Vaccine* 10: 43–48.
41. Novotny, P., Chubb, A. P., Cownley, K., and Charles, I. G. (1991). Biological and protective properties of the 69 kDa outer membrane protein of *Bordetella pertussis*: a novel formulation for an acellular vaccine. *J. Infect. Dis.* 164: 114–122.
42. Shahin, R. D., Brennan, M. J., Li. Z. M., Meade, B. D., and Manclark, C. R. (1990b). Characterization of the protective capacity and immunogenicity of the 69 kDa outer membrane protein of *Bordetella pertussis*. *J. Exp. Med.* 171: 63–73.
43. Robinson, A., Irons, L. I., and Ashworth, L. A. E. (1985a). Pertussis vaccine: present status and future prospects. *Vaccine* 8: 11–22.
44. Robinson, A., Ashworth, L. A. E. Baskerville, A., and Irons, L. I. (1985b). Protection against intranasal infection of mice with *Bordetella pertussis*. *Develop. Biol. Stand.* 61: 165–172
45. Robinson, A., Gorrige, A. R., Funnell, S. G. P., and Fernandez, M. (1989b). Serospecific protection of mice against in infection with *Bordetella pertussis*. *Vaccine* 7: 321–324.
46. Sato, Y., Kimura, M., and Fukumi, H. (1984a). Development of a pertussis component vaccine in Japan. *Lancet* i: 122–126.
47. Kimura, M. (1991). Japanese clinical experiences with acellular pertussis vaccines. *Develop. Biol. Standard.* 73: 5–9.
48. Ad Hoc Group for the Study of Pertussis Vaccines (1988). Placebo-controlled trial of two acellular vaccines in Sweden-protective eficacy and adverse effects. *Lancet* i: 955–960.
49. Olin, P., Storsaeter, J., and Romanus, V. (1989). The efficacy of acellular pertussis vaccine. *JAMA* 261:560.
50. Storsaeter, J., Hallander, H., Farrington, C. P., Olin, P., Moliby, R., and Miller, E. (1990). Secondary analyses of the efficacy of two acellular pertussis vaccines evaluated in a Swedish phase III trial. *Vaccine* 8: 457–462.
51. Storsaeter, J., and Olin, P. (1992). Relative efficacy of two acellular pertussis vaccines during three years of passive surveillance. *Vaccine:* 10: 142–144.
52. Tan, L. U. T., Fahim R. E. F., Jackson, G., Phillips, K., Wah, P., Alkema, D., Zobrist, G., Herbert, A., Boux, L, Chong, P., Harjee, N., Klein, M., and Vose, J. (1991). A novel process for preparing an acellular pertussis vaccine composed of non-pyrogenic toxoids of pertussis toxin and filamentous haemagglutonin. *Molec. Immunol.* 28: 251–255.
53. Sekura, R. D., Zhang, Y., Roberson, R., Acton, B., Trollfors, B., Tolson, N., Siloach, J., Bryla, D., Muir-Nash, J., Koeller, D., Schneerson, R., and Robbins, J. B. (1988). Clinical, metabolic, and antibody responses of adult volunteers to an investigation vaccine composed of pertussis toxin inactivated by hydrogen peroxide. *J. Pediatr.* 113: 807–813.
54. Winberry, L., Walker, R., Cohen, N., Todd, C., Sentissi, A., and Siber, G. (1988), Evaluation of a new method for inactivating pertussis toxin with tetranitromethane. *International Workshop on Bordetella pertussis*, Rocky Mountain Laboratories, Hamilton, Mont.
55. Sekura, R. D. et al. (1993), *J. Biol. Chem.* 258: 14647–14651.
56. Irons, L. I. et al. (1979), *Biochem. Biophys. Acta* 580: 175–185.
57. Munoz, J. J. et al. (1981), *Infect. Immun.* 33: 820–826.
58. Cowell, J. L. et al. (1980), Seminar on Infectious Diseases 4: 371–379.
59. Salmer, J. C. (1984) *Acta Path. Microbial. Immunol. Scand. Sect. C,* 92: 279–284.
60. Lockhoff, O. (1991) Glycolipids as Immunomodulators: Synthesis and Properties, *Chem. Int. Ed. Engl.* 30: 1611–1620.
61. Nixon-George, A., Moran, T., Dionne, G., Penney, C. L., Lafleur, D., Bona, C. A. (1990) The adjuvant effect of stearyl tyrosine on a recombinant subunit hepatitis B surface antigen. *J. Immunol.* 144: 4798–4802.
62. Siber, G. R., Thakrar, N., Yancey, B. A., Herzog. L., Todd, C., Cohen, N., Sekura, R. D., Lowe, C. U. (1991). Safety and immunogenicity of hydrogen peroxide-inactivated pertussis toxoid in 18-month-old children. *Vaccine* 9: 735–740.
63. Siber, G., Winberry, L., Todd, C., Samore, M., Sentissi, A., and Cohen, N. (1988). Safety and immunogenicity in adults of pertussis toxoid inactivated with tetronitromethane. In: *International Workshop on Bordetella pertussis*, Rocky Mountain Laboratories, Hamilton, Mont.
64. Edwards, K. M., Bradley, R. B., Decker, M. D., Palmer, P. S., Van Savage, J., Taylor, J. C., Dupont, W. D., Hager, C. C., and Wright, P. F. (1989). Evaluation of a new highly purified pertussis vaccine in infants and children. *J. Infect. Dis.* 160: 832–837.
65. Rutter, D. A., Ashworth, L. A. E., Day, A., Funnell, S., Lovell, F., and Robinson, A. (1988). Trial of new acellular pertussis vaccine in healthy adult volunteers. *Vaccine* 6: 29–32.
66. Blumberg, D. A., Mink, C. A. M, Cherry, J. D., Johnson, C., Garber, R., Plotkin, S. A., Watson, B., Ballanco, G. A., Daum R. S., Sullivan B., Townsend, T. R. Brayton, J., Gooch, W. M., Nelson, D. B., Congeni, B. L., Prober, C. G., Hackell, J. G., Dekker, C. L., Christenson, P. D., and the APDT Vaccine Study Group (1991). Comparison of acellular and whole cell pertussis-component diphtheria-tetanus-pertussis vaccines in infants. *J. Pediatr.* 119: 194–204.
67. Englund, J. A., Glezen, W. P. and Barreto, L. (1992a). Controlled study of a new five-component acellular pertussis vaccine in adults in young children. *J. Inf. Dis.* 166: 1436–1441.
68. Zealey, G., Loosmore, S., Yacoob, R., Klein, M., Vaccine Research, Vol. 1, pp. 413–427.
69. Baker J D, Halperin S A, Edwards K, Miller B. Decker M, Stephens D. Antibody response to *Bordetella pertussis* antigens after immunization with American and Canadian whole cell vaccines *J. pediatr.* 1992, 121:523–527.
70. Halperin S A. Eastwood B J. Langley J M. Immune responses to pertussis vaccines concurrently administered with viral vaccines. Ann NY Acad Sci. 1995, 754: 89–96.
71. Halperin S A, Langley J M. Eastwood B J. Effect of inactivated poliovirus vaccine on the antibody response to *Bordetella pertussis* antigens when combined with diphtheria-pertussis-tetanus vaccine. Clin. Infect. Dis. 1996; in press
72. Ferreccio C., Clemens J. Avendano A. et al. The clinical and immunogenic response of Chilean infants to Haemophilus influenzae type b polysaccharide tetanus protein conjugate vaccine coadministered in the same syringe with diptheria-tetanus toxoide-pertussis vaccine at two, four and six months of age. Pediatr. Infect. Dis. J. 1991; 10:761–771.

73. Clemens J. Ferreccio C., Levine M. et al. Impact of *Haemophilus influenzae* typ b polysaccharide-tetanus protein conjugate vaccine on responses to concurrently administered diphetheria-tetanus pertussis vaccine. JAMA 1992; 267:673–8.
74. Scheifele D. Barreto L. Meekison W. et al. Can *Haemophilus influenaze* vaccine be combined with diptheria and tetanus toxoids. Can Med Assoc. J. 1993; 149: 1105–16.
75. Gold R., Scheifele D., Barreto L. et al. Safety and immunogenicity of *Haemophilus influnzae* vaccine (tetanus toxoid conjugate) administered concurrently or combined with diptheria and tetanus toxoids, pertussis vaccine and inactivated poliomyelitis vaccine to healthy infants at two, four and six months of age. Pediatr. Infect. Dis J. 1994; 13: 348–55.
76. Shinefield H. Black S, Ray P, Lewis E. Fireman B., Hohenboken, hackell J G. Safety of combined acellular pertussis vaccine in infants [abstract no G72]. In: program and Abstracts of the 35th Interscience Conference on Antimicrobiols and Chemotherapy. Washington, D.C.; American Society of Microbiology 1995: 171.
77. Greenberg D P, Wong V K, Partridge S, Howe B J, Fing J. Ward J L. Evaluation of a new combination vaccine that incorporates diptheria-tetanus-acellular pertussis, hepatitis b, and *Haemophilus influenzae* type b conjugate vaccines [Abstract no G70] In program and Abstracts of the 35th Interscience Conference on Antimicrobiols and Chemotherapy. Washington, D.C.; American Society of Microbiology 1995: 170.
78. Wassilak S G F, Orenstein W A, Tetanus, In Plotkin S A, Mortimer E A, Jr., eds. Vaccines, WB Saunders Company, Philadelphia, 1988; 45–73.
79. Gustaffson et al, New England J. Medicine, 1996, vol. 334. Pp 349–355.
80. Mortimer E A Jr., Diphtheria Toxoid, In Plotkin S A, Mortimer E A, Jr., eds, Vaccines, WB Saunders Company, Philadelphia, 1988; 31–44.
81. Varughese P: *Haemophilus Influenzae* infection in Canada, 1969–1985. Can Dis Wkly Rep 1986; 12:37–43.
82. Schelfele D, Gold R, Law B., et al: Decline in *Haemophilus Influenzae* type b invasive infections at five Canadian pediatric centres. Can Commun Dis Rep 1993; 19:88–91
83. Scheifele D., Barreto L., Meekison W. et al.: Can *Haemophilus influenzae* type b-tetanus toxoid conjugate vaccine be combined with diphtheria toxoid-pertussis vaccine-tetanus toxoid? Can Med Assoc J 1993,149: 1105–1112
84. Gold R, Scheifele D, Barreto L et al.: Safety and Immunogenicity of *Haemophilus Influenzae* type b vaccine (tetanus toxoid conjugate) administered concurrently or combined with diphtheria and tetanus toxoids, pertussis vaccine and inactivated poliomyelitis vaccines to healthy infants at two, four and six months of age. Pediatric Infectious Diseases Journal 1994; 13:348–55
85. Scheifele D, Gold R et al.: Canada Communicable Disease Report 22-3, F1–F3, Feb. 1, 1996.

What we claim is:

1. A multi-valent immunogenic composition for conferring protection in a host against disease caused by infection by *Bordetella pertussis, Clostridium tetani, Corynebacterium diphtheriae* and poliovirus, consisting essentially of:
    (a) pertussis toxoid in an amount of about 5 to about 30 µg of nitrogen, filamentous haemagglutinin in an amount of about 5 to about 30 µg of nitrogen, pertactin in an amount of about 3 to about 15 µg of nitrogen and agglutinogens in an amount of about 1 to about 10 µg of nitrogen, said pertussis toxoid, filamentous haemagglutinin, pertactin and agglutinogens being present in purified form,
    (b) tetanus toxoid in an amount of about 1 to about 10 Lfs,
    (c) diphtheria toxoid in an amount of about 10 to about 20 Lfs, and
    (d) inactivated polio virus in the form of a mixture of inactivated polioviruses 1, 2 and 3 in an amount:
        about 20 to about 50 D antigen units of poliovirus type 1
        about 5 to about 10 D antigen units of poliovirus type 2
        about 20 to about 50 D antigen units of poliovirus type 3,
    said respective quantities of components (a), (b), (c) and (d) being determined on the basis of a single human dose, said immunogenic composition being formulated as a vaccine for in vivo administration to a host wherein the individual components of the composition are formulated such that the immunogenicity of individual components is not impaired by other individual components of the composition.

2. The immunogenic composition of claim 1 further comprising an adjuvant.

3. The immunogenic composition of claim 2 wherein the adjuvant is aluminum phosphate.

4. The immunogenic composition of claim 1 containing about 20 µg nitrogen of pertussis toxoid, about 20 µg nitrogen of filamentous haemagglutinin, about 5 µg nitrogen of agglutinogens and about 3 µg nitrogen of pertactin in a single human dose.

5. The immunogenic composition of claim 4 wherein said tetanus toxoid component (b) is present in an amount of about 5 Lfs and diphtheria toxoid component (c) is present in an amount of about 15 Lfs.

6. The immunogenic composition of claim 5 wherein said inactivated polio virus comprises a mixture of inactivated polio viruses types 1, 2 and 3 in the proportions
    about 40 D antigen units of poliovirus type 1
    about 8 D antigen units of poliovirus type 2
    about 32 D antigen units of poliovirus type 3 in a single human dose.

7. A vaccine composition, comprising, per 0.5 ml dose,
    20 µg of pertussis toxoid
    20 µg of filamentous haemagglutinin
    5 µg of fimbrial agglutinogens 2 and 3
    3 µg of pertactin outer membrane protein
    15 Lf diphtheria toxoid
    5 Lf tetanus toxoid
    poliovirus type 1 40 D antigen units
    poliovirus type 2 8 D antigen units
    1.5 µg aluminum phosphate and wherein said pertussis toxoid, filamentous haemagglutinin, fimbrial agglutinogens, pertactin, diphtheria toxoid, tetanus toxoid and poliovirus are formulated such that the immunogenicity of individual components is not impaired by other individual components of the composition.

8. The composition of claim 7 further comprising, per 0.5 ml dose:
    0.6% 2-phenoxyethanol.

9. A method of protecting a human host against disease caused by infection by *Bordetella pertussis, Clostridium tetani, Corynebacterium diphtheriae* and poliovirus, which comprises administering to the host an immunoeffective amount of the immunogenic composition of claim 1.

10. The method of claim 9 wherein the host is a child.

* * * * *